US008778347B2

(12) United States Patent
Kachurin et al.

(10) Patent No.: US 8,778,347 B2
(45) Date of Patent: Jul. 15, 2014

(54) FLUORESCENT NEUTRALIZATION AND ADHERENCE INHIBITION ASSAYS

(75) Inventors: Anatoly Kachurin, Orlando, FL (US); Olga Kachurina, Orlando, FL (US); Vaughan Wittman, Oviedo, FL (US); Tenekua Tapia, Orlando, FL (US)

(73) Assignee: Sanofi Pasteur Vaxdesign Corp., Orlando, FL (US)

( * ) Notice: Subject to any disclaimer, the term of this patent is extended or adjusted under 35 U.S.C. 154(b) by 777 days.

(21) Appl. No.: 12/616,659

(22) Filed: Nov. 11, 2009

(65) Prior Publication Data

US 2010/0120020 A1 May 13, 2010

Related U.S. Application Data

(60) Provisional application No. 61/113,263, filed on Nov. 11, 2008.

(51) Int. Cl.

| | |
|---|---|
| ***A01N 63/00*** | (2006.01) |
| ***A61K 39/42*** | (2006.01) |
| ***A61K 39/12*** | (2006.01) |
| ***A61K 45/00*** | (2006.01) |
| ***C12Q 1/70*** | (2006.01) |
| ***G01N 33/53*** | (2006.01) |
| ***C12Q 1/02*** | (2006.01) |
| ***C12N 7/00*** | (2006.01) |
| ***G01N 21/76*** | (2006.01) |
| *A61K 49/00* | (2006.01) |

(52) U.S. Cl.
USPC .................. 424/159.1; 424/204.1; 424/281.1; 424/93.1; 424/93.6; 435/5; 435/7.1; 435/29; 435/235.1; 436/172

(58) Field of Classification Search
None
See application file for complete search history.

(56) References Cited

U.S. PATENT DOCUMENTS 4,908,305 A 3/1990 Snyder

OTHER PUBLICATIONS

Nichols et al., Use of FITC-labeled influenza virus and flow cytometry to assess binding and internalization of virus by monocytes-macrophages and lymphocytes, 1992, Archives of Virology, vol. 130, pp. 441-455.*

Earl P.L., et al., Development and Use of a Vaccinia Virus Neutralization Assay Based on Flow Cytometric Detection of Green Fluorescent Protein, Journal of Virology, Oct. 2003, p. 10684-10688.

Kraus A.A., et al., Comparison of Plaque- and Flow Cytometry-Based Methods for Measuring Dengue Virus Neutralization, Journal of Clinical Microbiology, Nov. 2007, p. 3777-3780.

Bernard J. Cohen, et al., Plaque reduction neutralization test for measles antibodies: Description of a standardised laboratory method for use in immunogenicity studies of aerosol vaccination, Vaccine (2007) 26, 59-66.

R.E. Wooley and J. Brown, Correlation of Cytopathic Effect, Fluorescent-Antibody Microneutralization, and Plaque Reduction Test Results for Determining Avian Infectious Bronchitis Virus Antibodies, Journal of Clinical Microbiology, Mar. 1977, p. 361-364.

Iana H. Haralambieva et al., Development of a Novel Efficient Fluorescence-Based Plaque Reduction Microneutralization Assay for Measles Virus Immunity, Clinical and Vaccine Immunology, Jul. 2008, p. 1054-1059, vol. 15, No. 7.

International Search Report dated Jun. 28, 2010 for PCT/US2009/064026.

Cosma, A. et al., Neutralization Assay Using a Modified Vaccinia Virus Ankara Vector Expressing the Green Fluorescent Protein Is a High-Throughput Method to Monitor the Humoral Immune Response against Vaccinia Virus, Clinical and Diagnostic Laboratory Immunology, 2004, vol. 11, No. 2, pp. 406-410.

Kampani, K. et al., A Novel High Throughput Quantum Dot-Based Fluorescence Assay for Quantitation of Virus Binding and Attachment, Journal of Virological Methods, 2007, vol. 141, No. 2, pp. 125-132.

Supplementary European Search Report, dated Feb. 13, 2013, from the European Patent Office in corresponding European Patent Application No. 09826670.3.

* cited by examiner

*Primary Examiner* — Benjamin P Blumel
(74) *Attorney, Agent, or Firm* — Roylance, Abrams, Berdo & Goodman, L.L.P.

(57) ABSTRACT

The present invention comprises rugged, inexpensive, reliable, and sensitive laboratory assays of antibody-based viral neutralization activity and antibody-based viral adherence inhibition activity. The assays use inactivated, fluorescently-labeled virus, allowing the tests to be performed without extensive safety precautions. The interaction of the labeled virus with target cells is monitored using flow cytometric methods. A preferred embodiment uses simple and inexpensive flow cytometry methodologies and equipment, such as bead array readers used as simplified flow cytometers. The assays are rapid, taking no longer than a few hours and are readily conducted by a trained technician. The assays are sensitive because they use labeled viruses at low concentrations and determine neutralizing and blocking capacity of sera and antibody at low concentrations. The methods are appropriate for high-throughput screening of large panels of samples.

15 Claims, 20 Drawing Sheets

| | Region 11 | | Region 17 | | Region 25 | | | |
|---|---|---|---|---|---|---|---|---|
| | MFI | Events | MFI | Events | MFI | Events | Total gated | Region / Gates Efficiency |
| Zero anti-PE:QSY | 4718.5 | 52 | 3278 | 25 | 4940 | 137 | 579 | 37% |
| 10 ug/ml anti-PE:QSY | 1840.5 | 90 | 1589 | 15 | 1753 | 137 | 692 | 35% |
| 30 ug/ml anti-PE:QSY | 2039 | 45 | 1158 | 33 | 1643 | 324 | 998 | 40% |

BioPlex MFI signal is calculated as a pooled average over three regions:

**<MFI for Zero anti-PE:QSY> = (4718.5*52 + 3278*25 + 4940*137) / (52 + 25 + 137) = 4692.02**

| Assay | Blocking titer | Virus dilution |
|---|---|---|
| fmNt | 520 +-180 | 1 to 100 |
| fADI | 32700 +-18500 | 1 to 3200 |

FLUORESCENT NEUTRALIZATION AND ADHERENCE INHIBITION ASSAYS

CROSS-REFERENCE TO RELATED APPLICATIONS

This application claims benefit under 35 U.S.C. §119(e) of U.S. Patent Application No. 61/113,263, filed Nov. 11, 2008, which is hereby incorporated herein by reference in its entirety.

BACKGROUND OF THE INVENTION

The ability of an anti-viral pathogen vaccine to produce an effective antibody response is typically evaluated in various types of virus neutralization tests or assays. Common features of such tests include monitoring the level of infectivity of the virus (natural or attenuated) in a standardized target cell culture, and evaluating the reduction in infectivity of the virus after incubation with the tested serum/sera or antibody solution(s) of interest.

The dilution of a serum or antibody (Ab) solution that provides 50% or more reduction of infectivity is referred to as the 'neutralization titer' (Niedrig et al. (2008) *Clin. Vaccine Immunol.* 15, 177; Guidelines for Plaque-Reduction Neutralization Testing of Human Antibodies to Dengue Viruses, WHO, 2007). Virus neutralization assays are widely used worldwide for a variety of viruses, from the relatively common, such as influenza and herpes simplex, to the most feared and dangerous viruses, such as smallpox, yellow fever, and dengue hemorrhagic fever (Niedrig et al. (2008) *Clin. Vaccine Immunol.* 15, 177; Guidelines for Plaque-Reduction Neutralization Testing of Human Antibodies to Dengue Viruses, WHO, 2007).

In the virology community, the plaque reduction neutralization test (PRNT) is generally considered the gold standard of neutralization assays for studying anti-viral humoral immune responses (Niedrig et al. (2008) *Clin. Vaccine Immunol.* 15, 177; Guidelines for Plaque-Reduction Neutralization Testing of Human Antibodies to Dengue Viruses, WHO, 2007; Roukens et al. (2008) *PLoS ONE,* 3, e1993; Niedrig et al. (1999) *Trop. Med. Int. Health* 4, 867). In the PRNT, a highly diluted virus culture, with or without various concentrations of a test serum or an antibody solution, is added to a culture of a confluent layer of target cells, and the level of infectivity is measured by the number of cell-free lacunas appearing in the culture after a period of incubation (typically a few days).

Currently, various more recent immunosorption methods compete with the PRNT, such as the immunofluorescent assay (IFA) (Kraus et al. (2007), *J. Clin. Microbiol.* 45, 3777; Niedrig et al. (1999) *Trop. Med. Int. Health* 4, 867; Groot & Riberiro (1962) *Bull. WHO* 27, 699; Vazquez et al. (2003) *J. Virol. Methods* 110, 179; Barry et al. (1991) *Am. J. Trop. Med. Hyg.* 44, 79; Deubel et al. (1983) *Am. J. Trop. Med. Hyg.* 32, 565)), where the infectivity level of virus is evaluated using fluorescently-labeled, virus-specific antibodies applied to fixed samples of target cells after incubation with live virus and washing. The IFA, although sensitive and virus-specific, remains under consideration, because the antibody titers from the IFA often do not correlate well with those from the PRNT (Niedrig et al. (1999) *Trop. Med. Int. Health* 4, 867; Groot & Riberiro (1962) *Bull. WHO* 27, 699; Vazquez et al. (2003) *J. Virol. Methods* 110, 179; Barry et al. (1991) *Am. J. Trop. Med. Hyg.* 44, 79; Deubel et al. (1983) *Am. J. Trop. Med. Hyg.* 32, 565).

A microneutralization method similar to the IFA, but using enzyme-linked immunosorption, was developed in Centers for Disease Control and Prevention (CDC). In this assay, the level of virus infectivity with or without tested sera is estimated by measuring nuclear protein (NP) of the avian influenza virus expressed in the target MDCK cells by staining the permeabilized fixed cells with the NP-specific monoclonal Ab labeled with horseradish peroxidase (HRP) (Rowe et al. (1999) *J. Clin. Microbiol.* 37, 937-943).

Another direct microneutralization (MN) assay is also practiced by the World Health Organization (WHO). In the MN assay, a confluent layer of target cells is infected with a diluted virus culture either in the presence or absence of a test serum/sera or antibody solution(s) of interest, and the rate of virus reproduction is evaluated by measuring released virus concentrations with a standard hemagglutination assay (HA) technique. The assay is described in the "WHO Manual on Animal Influenza Diagnosis and Surveillance," (WHO/CDS/CSR/NCS/2002.5 Rev. 1) and may be found at the website beginning with "www." and ending with "who.int/vaccine_research/diseases/influenza/WHO_manual_on_animal-diagnosis_and_surveillance__2002__5.pdf". The protocol is simple and straightforward, although use of the HA technique presents certain limitations to the sensitivity of the method.

In general, the PRNT, IFA and MN have several complicating features:

- Use of live virus raises safety and personnel protection issues.
- Incubation of the target cells with live virus often requires significant time (up to ~5-7 days) to allow for infection to properly develop and infectivity to be reliably evaluated, making the tests lengthy and cumbersome.
- PRNT and IFA include multi-step fixation and staining protocols.

The use of modern flow cytometry techniques promises to significantly improve existing neutralization assays. In several published studies, viral infection of target cells in the presence or absence of a test serum/sera or antibody solution(s) of interest has been monitored by flow cytometric methods, where viruses or their cell-expressed protein components were stained with fluorescent tags (Kremser et al. (2004) *Anal. Chem.* 80, 7360; Sliva et al. (2004) *Virol. J.* 1, 14; You et al. (2006) *Int. J. Nanomedicine* 1, 59; Nichols et al. (1993) *Arch. Virol.* 130, 441; Klingen et al. (2008) *J. Virol.* 82, 237; Lonsdale et al. (2003) *J. Virol. Meth.* 110, 67-71; Wang et al. (2004) *J. Virol. Meth.* 120, 207-215; Collins & Buchholz (2005) *J. Virol. Meth.* 128, 192-197). For example, permeabilized target cells were stained with fluorescent antibodies specific to target-expressed viral proteins (Lonsdale et al. (2003) *J. Virol. Meth.* 110, 67-71), and green fluorescent protein (GFP) was incorporated in a recombinant vector and expressed in infected cells (You et al. (2006) *Int. J. Nanomedicine* 1, 59; Wang et al. (2004) *J. Virol. Meth.* 120, 207; Collins & Buchholz (2005) *J. Virol. Meth.* 128, 192; Earl et al. (2003), *J. Virol.* 77, 10684). Other examples include direct labeling of the virus (Kremser et al. (2004) *Anal. Chem.* 80, 7360; Klingen et al. (2008) *J. Virol.* 82, 237). Such labeling can be performed via direct chemical tagging with fluorochromes (Kremser et al. (2004) *Anal. Chem.* 80, 7360), or electrostatic attachment of quantum dots to the envelope proteins of the virus (Sliva et al. (2004) *Virol. J.* 1, 14). Nichols et al. (1993; *Arch. Virol.* 130, 441) and Klingen et al. (2008; *J. Virol.* 82, 237) developed an ingenious virus staining method, growing the virus on a pre-stained target cells.

These flow cytometric methods, however, also use live viruses or recombinant vectors, raising safety and other issues similar to those listed for PRNT and IFA assays. These methods, while sensitive and informative in the research setting, can hardly be considered appropriate as routine high-throughput assays. Thus, there is a continuing need for rugged, reliable, and sensitive laboratory methods for microneutralization assays.

SUMMARY OF THE INVENTION

Addressing the problems with existing assays, the present invention comprises a rugged, reliable, and sensitive laboratory method for a virus neutralization assay, characterized by the following:

- Use of inactivated, fluorescently-labeled virus, allowing the tests to be performed without extensive safety precautions.
- Interaction of the labeled virus with the target cells, monitored by flow cytometric methods. A preferred embodiment uses the simplest and least expensive flow cytometry methodologies and equipment. A more preferred embodiment uses a bead array reader, such as a BioPlex, as a simplified flow cytometer.
- The assay is rapid, taking no longer than a few hours (normally, ~1.5-4 h) and is readily conducted by a trained technician.
- The assay is sensitive; that is, it uses labeled viruses at low concentrations and measures blocking/neutralizing capacity of sera and antibodies at low concentrations.
- The assay is appropriate for automation and high-throughput screening of sera and culture fluids.
- The assay is inexpensive, using, for example, the rugged BioPlex bead array platform as a simplified flow cytometer at a cost ~20% of a regular flow cytometer such as, for example, a BD LSR II (BD Biosciences).

Embodiments of the present invention comprise affinity fluorescent labeling of the virus used in the fmNt (fluorescence-based micro neutralization) assay. For example, the virus is sparsely labeled with biotinylated virus-specific antibody possessing low neutralizing capacity, and streptavidin-phycoerythrin conjugate is attached to the biotins. This method can work equally well labeling live or inactivated virus, in pure culture or one containing high levels of contaminants. In another embodiment, the inactivated virus is sparsely biotinylated, and streptavidin-phycoerythrin conjugate is attached to the biotins.

In another embodiment, for example, a bead array reader, such as a BioPlex, is used as a simplified flow cytometer to detect fluorescence of the labeled virus engulfed by, or attached to, target cells. Using a bead array reader, such as a BioPlex, instead of a flow cytometer can reduce the cost of the assay by ~5-fold and allows working with lower numbers of target cells in the sample.

Another embodiment of the present invention involves "addressed" affinity quenching of the phycoerythrin fluorescence using an anti-phycoerythrin antibody coupled with the QSY-9 quenching dye. This method increases the efficiency of quenching surface-bound fluorescence, which is undesirable in fluorescence-based microneutralization (fmNt) experiments.

Another embodiment of the present invention comprises a "Fluorescent Adherence Inhibition Assay" (fADI), a method to measure the capacity of a virus-specific antibody or anti-virus sera to block adherence of the virus to the surface of target cells. The method comprises a combination of a hemagglutination inhibition assay (HAI) and fluorescence microneutralization assay and features at least about a 10-fold improvement in sensitivity versus previous fluorescence-based microneutralization assays (fmNt) and hemagglutination inhibition assays (HAI).

The present invention is also directed to the following specific embodiments. In a first embodiment, the invention is directed to a method for determining a neutralizing activity of a test antibody, comprising:

a) incubating a test antibody with a fluorescently-labeled virus to form a mixture, b) incubating a population of target cells with the mixture of a) under conditions permitting endocytosis of the labeled virus by the target cells, c) measuring fluorescence of labeled virus endocytozed by the target cells, and d) comparing the fluorescence measured in c) with fluorescence of fluorescently-labeled virus measured in a control experiment where the labeled virus was not incubated with a test antibody, thereby determining a neutralizing activity of a test antibody.

In a second embodiment, the present invention is directed to a method for determining a neutralizing activity of a test antibody, comprising:

a) incubating a test antibody with a fluorescently-labeled virus to form a mixture, b) incubating a population of target cells with the mixture of a) under conditions permitting endocytosis of the labeled virus by the target cells, c) incubating the population of target cells of b) with a quencher of fluorescence of labeled virus bound to the surface of the cells, d) measuring fluorescence of labeled virus endocytozed by the target cells, and e) comparing the fluorescence measured in d) with fluorescence of fluorescently-labeled virus measured in a control experiment where the labeled virus was not incubated with a test antibody, thereby determining a neutralizing activity of a test antibody.

In one aspect, the quencher of fluorescence of the labeled virus bound to the surface of the cells is a protease. In another aspect, the quencher of fluorescence of the labeled virus bound to the surface of the cells is an antibody that specifically binds the fluorescent label of the labeled virus, wherein the antibody is conjugated to at least one quenching compound, and wherein the quenching compound is a fluorescent quenching dye. In a preferred aspect, the labeled virus is a virus having a biotinylated antibody bound thereto wherein the antibody is conjugated to a phycoerythrin:streptavadin conjugate, and the antibody that specifically binds the fluorescent label of the labeled virus is a phycoerythrin-specific antibody conjugated to quenching dye QSY-9, quenching dye QSY-21, or both quenching dyes. The quenching dye may also be trypan blue or crystal violet.

In a third embodiment, the present invention is directed to a method for determining a neutralizing activity of a test antibody, comprising:

a) incubating a test antibody with a fluorescently-labeled virus to form a mixture, b) incubating a population of target cells with the mixture of a) under conditions permitting endocytosis of the labeled virus by the target cells, c) incubating the population of target cells of b) with a quencher of fluorescence of labeled virus bound to the surface of the cells, d) staining the population of target cells of c) with a dye, e) measuring fluorescence of labeled virus endocytozed by the target cells, and f) comparing the fluorescence measured in e) with fluorescence of fluorescently-labeled virus measured in a control experiment where the labeled virus was not incubated with a test antibody, thereby determining a neutralizing activity of a test antibody.

In one aspect, the quencher of fluorescence of the labeled virus bound to the surface of the cells is a protease. In another aspect, the quencher of fluorescence of the labeled virus bound to the surface of the cells is an antibody that specifically binds the fluorescent label of the labeled virus, wherein the antibody is conjugated to at least one quenching compound, and wherein the quenching compound is a fluorescent quenching dye. In a preferred aspect, the labeled virus is a virus having a biotinylated antibody bound thereto wherein the antibody is conjugated to a phycoerythrin:streptavadin conjugate, and the antibody that specifically binds the fluorescent label of the labeled virus is a phycoerythrin-specific antibody conjugated to quenching dye QSY-9, quenching dye QSY-21, or both quenching dyes. In a further aspect, the quencher is dye, and the dye is trypan blue or crystal violet.

In another aspect, the population of cells is stained with a dye having a weak red and infrared fluorescence to facilitate classification of the cells in a BioPlex bead array reader. Alternatively, the population of cells is stained with a dye that quenches the fluorescent label of the labeled virus. In certain embodiments, the dye serves both functions. In a specific aspect, the staining dye is trypan blue or crystal violet.

In a fourth embodiment, the present invention is directed to a method for determining an inhibitory activity of a test antibody, comprising:

a) incubating a test antibody with a fluorescently-labeled virus to form a mixture, b) incubating a population of target cells with the mixture of a) under conditions subduing endocytosis and permitting cell surface adherence of the labeled virus to the target cells, c) measuring fluorescence of labeled virus adhered to the surface of the target cells, and d) comparing the fluorescence measured in c) with fluorescence of fluorescently-labeled virus measured in a control experiment where the labeled virus was not incubated with a test antibody, thereby determining an inhibitory activity of a test antibody.

In a fifth embodiment, the present invention is directed to a method for determining an inhibitory activity of a test antibody, comprising:

a) incubating a test antibody with a fluorescently-labeled virus to form a mixture, b) incubating a population of target cells with the mixture of a) under conditions subduing endocytosis and permitting cell surface adherence of the labeled virus to the target cells, c) staining the population of target cells of b) with a dye, d) measuring fluorescence of labeled virus adhered to the surface of the target cells, and e) comparing the fluorescence measured in d) with fluorescence of fluorescently-labeled virus measured in a control experiment where the labeled virus was not incubated with a test antibody, thereby determining an inhibitory activity of a test antibody.

In one aspect, the population of cells is stained with a dye having a weak red and infrared fluorescence to facilitate classification of the cells in a BioPlex bead array reader. Alternatively, the population of cells is stained with a dye that quenches the fluorescent label of the labeled virus. In certain embodiments, the dye serves both functions. In a specific aspect, the staining dye is trypan blue or crystal violet.

In each of the embodiments of the invention, the labeled virus may be a virus selected from the group consisting of adenoviruses, filoviruses, flaviviruses, herpesviruses, poxviruses, parvoviruses, reoviruses, picornaviruses, togaviruses, orthomyxoviruses, rhabdoviruses, retroviruses, and hepadnaviruses, conjugated to a fluorescent label.

In a preferred aspect, the labeled virus comprises an influenza virus conjugated to a fluorescent label. In an equally preferred aspect, the labeled virus comprises an influenza A virus conjugated to a fluorescent label. In a further preferred aspect the labeled virus comprises an H1N1 influenza virus or H3N2 influenza virus or H5N1 influenza virus conjugated to a fluorescent label. In an additionally preferred aspect the labeled virus is Marburg hemorrhagic fever virus-like particle or gamma-inactivated Ebola virus conjugated to a fluorescent label. In each aspect, the fluorescent label may be phycoerythrin or allophycocyanin.

Alternatively, in each of the embodiments of the invention, the labeled virus may be a biotinylated virus selected from the group consisting of adenoviruses, filoviruses, flaviviruses, herpesviruses, poxviruses, parvoviruses, reoviruses, picornaviruses, togaviruses, orthomyxoviruses, rhabdoviruses, retroviruses, and hepadnaviruses, conjugated to a streptavadin:fluorescent label. In a preferred aspect, the labeled virus comprises a biotinylated influenza virus conjugated to a streptavadin:fluorescent label. In an equally preferred aspect, the labeled virus comprises a biotinylated influenza A virus conjugated to a streptavadin:fluorescent label. In a further preferred aspect, the labeled virus comprises a biotinylated H1N1 influenza virus or H3N2 influenza virus or H5N1 influenza virus conjugated to a streptavadin:fluorescent label. In an alternative aspect, the labeled virus comprises biotinylated Marburg virus-like particles (VLP) tagged with streptavidin-phycoerythrin conjugate. In another alternative aspect, the labeled virus comprises gamma-inactivated and biotinylated Ebola virus tagged with streptavidin-phycoerythrin conjugate. In each aspect, the fluorescent label may be phycoerythrin or allophycocyanin.

In addition, in each of the embodiments of the invention, the labeled virus may be a virus selected from the group consisting of adenoviruses, filoviruses, flaviviruses, herpesviruses, poxviruses, parvoviruses, reoviruses, picornaviruses, togaviruses, orthomyxoviruses, rhabdoviruses, retroviruses, and hepadnaviruses, bound by a fluorescent label:streptavadin-conjugated biotinylated antibody that specifically binds the virus. In a preferred aspect, the labeled virus comprises an influenza virus bound by a biotinylated antibody that specifically binds the virus and that has a fluorescent label:streptavadin conjugate bound thereto. In an equally preferred aspect, the labeled virus comprises an influenza A virus bound by a biotinylated antibody that specifically binds the virus and that has a fluorescent label:streptavadin conjugate bound thereto. Such antibodies include the biotinylated anti-influenza A H1 specific antibody #1307 and the biotinylated antibody is the biotinylated anti-influenza A H3 specific antibody #1317. In a further preferred aspect, the labeled virus comprises an H1N1 influenza virus or H3N2 influenza virus H5N1 influenza virus bound by a biotinylated antibody that specifically binds the virus and that has a fluorescent label:streptavadin conjugate bound thereto. In an alternative aspect, the labeled virus comprises betapropiolactone (BPL)-inactivated 'avian' influenza H5N1 virus bound by a biotinylated antibody that specifically binds the virus and that has a fluorescent label: streptavadin conjugate bound thereto. In an additional aspect, the labeled virus is Marburg hemorrhagic fever virus-like particle or gamma-inactivated Ebola virus bound by a biotinylated antibody that specifically binds the virus and that has a fluorescent label:streptavadin conjugate bound thereto. In each aspect, the fluorescent label may be phycoerythrin or allophycocyanin.

In each of the embodiments of the invention, the virus may be an inactivated or an attenuated virus. When inactivated, the virus may be inactivated using BPL, or UV or gamma irradiation. In an alternative aspect, the virus inactivation method can be any inactivation method that preserves the ability of the virus to adhere specifically to target cells.

In each of the embodiments of the invention, the population of target cells may be a mammalian cell line, an avian cell line, an amphibian cell line, or other cell line susceptible to viral attack. In one aspect, the population of target cells comprises a human cell line. In another aspect, the population of target cells comprises avian erythrocytes. In a further aspect, the population of target cells comprises a cell line selected from the group consisting of Madin-Darby canine kidney epithelial cells and Vero green monkey kidney epithelial cells.

In each of the embodiments of the invention, measuring of fluorescence may be through the use of a flow cytometer or a bead array reader. For example, a BioPlex-100, a BioPlex-200, a Luminex-100, or a Luminex-200 bead array reader may be used.

In each of the embodiments of the invention, the incubating of the target cells with the labeled virus may be at 4° C. or 37° C.

In each of the embodiments of the invention, the neutralizing activity of sera or an antibody is the blocking of entry of the labeled virus into the target cells.

In each of the embodiments of the invention, the blocking activity of sera or an antibody is blocking adherence of the labeled virus to the target cells, or blocking entry of the labeled virus into the target cells.

BRIEF DESCRIPTION OF THE FIGURES

FIG. 2A=incubation at room temperature. FIG. 2B=incubation at 37° C. "Virus, serum"=virus+replacement sera; "Virus, no serum"=virus+PBS; "Blank, serum"=no virus+replacement sera; "Blank, no serum"=no virus+PBS.

FIG. 3A=incubation at 4° C. FIG. 3B=incubation at 37° C.

FIG. 11A=AB #1301; FIG. 11B=AB #1074. All samples were read in duplicate.

FIG. 12A=Donor #355, pre-vaccination; FIG. 12B=Donor #355, post-vaccination; FIG. 12C=Donor #419, pre-vaccination; FIG. 12D=Donor #419, post-vaccination. All samples were read in duplicate.

FIG. 15A: Comparison of fluorescence of the target cells in the fmNt and fADI experiments in the presence ("AB #1301") or absence ("No AB") of the polyclonal anti-influenza A antibody #1301, ViroStat. FIG. 15B: Fluorescence of the target cells in the fADI experiment at different concentrations of the virus. The level of fluorescence acceptable in the BioPlex-assisted experiment shown as a dashed line corresponds to significantly higher dilutions of the virus than in the fmNt experiment. Affinity-labeled Solomon Islands H1N1 BPL-inactivated virus; MDCK target cells.

FIG. 17A=Donor #608, pre-vaccination; FIG. 17B=Donor #608, post-vaccination; FIG. 17C=Donor #145, pre-vaccination; FIG. 17D=Donor #145, post-vaccination. All samples were in duplicate. Affinity-labeled New Caledonia H1N1 BPL-inactivated virus; turkey erythrocytes as target cells.

FIG. 19A=Donor #608, pre-vaccination; FIG. 19B=Donor #608, post-vaccination. All samples were in duplicate. Affinity-labeled Wisconsin H3N2 BPL-inactivated virus; turkey erythrocytes were used as target cells.

DETAILED DESCRIPTION OF THE INVENTION

Figure 1:
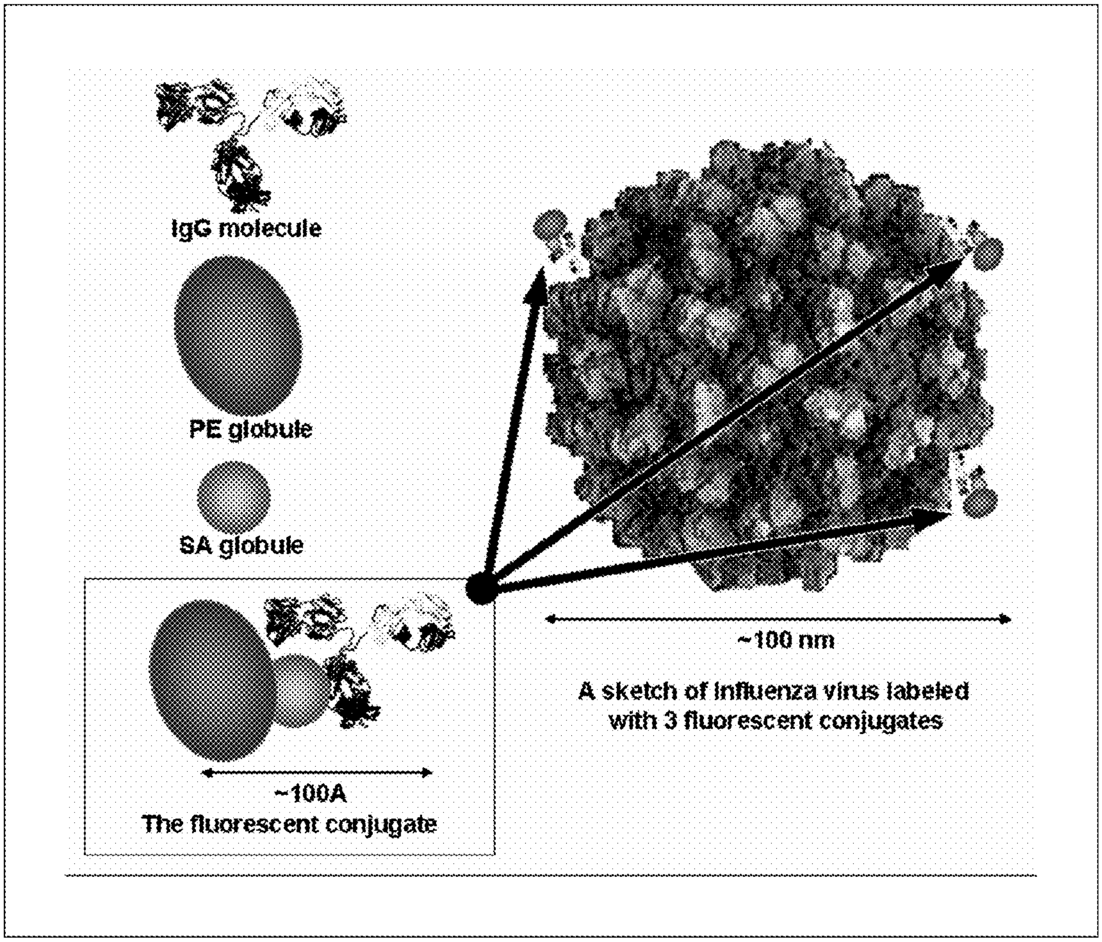
FIG. 1. Relative sizes of the affinity SA-PE (streptavidin: phycoerythrin conjugate) fluorescent probe and influenza virus. The affinity label represents a high-affinity biotinylated virus-specific antibody labeled with SA-PE fluorescent conjugate. All dimensions are shown approximately proportional to the natural size.

As discussed above in the Summary, the invention is primarily directed to two assays. In the first, second and third embodiments, the invention is directed to methods for determining the neutralizing activity of a test antibody. In the fourth and fifth embodiments, the invention is directed to methods for determining the inhibitory activity of a test antibody.

In the methods for determining the neutralizing activity of a test antibody, fluorescently-labeled virus is prepared or obtained, and a first portion of the labeled virus is incubated with serum/sera or antibody solution(s) of interest (the "test antibody"). A second portion of the labeled virus is incubated with a positive or negative control, such as an antibody that is known to bind (or not bind) the labeled virus or no antibody at all. A population of target cells are then prepared and incubated with the mixture of labeled virus and antibody under conditions permitting endocytosis of the labeled virus by the target cells. After a period of time, fluorescence of the labeled virus that has been endocytozed by the target cells is measured. Comparison of the fluorescence measured in the population of cells exposed to the labeled virus-test antibody against the fluorescence measured in the population of cells exposed to the labeled virus-control provides an indication of the ability of the test antibody to inhibit penetration of the target cells by the labeled virus, and thus the neutralizing activity of a test antibody.

The second and third embodiments of the invention provide aspects of the invention that reduce background fluorescence in the assay. In the second embodiment, after the population of cells is incubated with the mixture of labeled virus and antibody under conditions permitting endocytosis, the target cells are incubated with a quencher that quenches the fluorescence of any labeled virus that remains bound to the surface of the cells. In this manner, the signal produced by labeled virus that has been internalized can be more readily distinguished from the background signal produced by labeled virus that remains on the surface of the cell.

The third embodiment of the invention adds the additional step of staining the population of target cells with a dye. The dye facilitates classification of the cells in a BioPlex bead array reader, or the dye quenches the fluorescent label of the labeled virus. In certain embodiments, the dye serves both functions. When facilitating classification of the cells, the dye has a weak red and infrared fluorescence. Preferred dyes include trypan blue and crystal violet.

The fourth and fifth embodiments of the invention are similar to the first, second and third, but in contrast to assaying for endocytosis of the labeled virus into a target cells, these latter embodiment are directed to methods for determining the ability of a test antibody to block adherence of the virus to the surface of the cell. In the fourth embodiment, fluorescently-labeled virus is prepared or obtained, and a first portion of the labeled virus is incubated with serum/sera or antibody solution(s) of interest (the "test antibody"). A second portion of the labeled virus is incubated with a positive or negative control, such as an antibody that is known to bind (or not bind) the labeled virus or no antibody at all. A population of target cells are then prepared and incubated with the mixture of labeled virus and antibody under conditions that subdue endocytosis and permit cell surface adherence of the labeled virus to the target cells. After a period of time, fluorescence of the labeled virus that has adhered to the surface of the target cells is measured. Comparison of the fluorescence measured in the population of cells exposed to the labeled virus-test antibody against the fluorescence measured in the population of cells exposed to the labeled virus-control provides an indication of the ability of the test antibody to inhibit binding by the labeled virus to the surface of the target cells, and thus the inhibitory activity of a test antibody.

The fifth embodiment of the invention adds the additional step of staining the population of target cells with a dye. The dye facilitates classification of the cells in a BioPlex bead array reader, or the dye quenches the fluorescent label of the labeled virus. In certain embodiments, the dye serves both functions. When facilitating classification of the cells, the dye has a weak red and infrared fluorescence.

As used in the various embodiments and aspects of the invention, the quencher of surfaced-localized labeled virus may be any means that quenches surface fluorescence alone, without reducing the fluorescence of internalized labeled virus. Suitable quenchers include proteases specific for the fluorescent label. In a preferred aspect, the quencher is an antibody that specifically recognizes and binds to the fluorescent label of the virus. Such antibodies are conjugated to at least one quenching compound. As indicated above, suitable quenching compounds include dyes, such as quenching dye QSY-9 (Invitrogen) and quenching dye QSY-21. The antibodies may be conjugated to more than one dye.

There are few limitations of the identity of the virus that may be used in the embodiments and aspects of the invention. For example, the virus may be selected from among the adenoviruses, filoviruses, flaviviruses, herpesviruses, poxviruses, parvoviruses, reoviruses, picornaviruses, togaviruses, orthomyxoviruses, rhabdoviruses, retroviruses, and hepadnaviruses. In a preferred aspect, the virus comprises an influenza virus, such as an influenza A virus. In a equally preferred aspect the virus comprises the H1N1 influenza virus or H3N2 influenza virus or H5N1 'avian' influenza virus. In another preferred aspect, the virus comprises Marburg virus-like particles (VLPs) or gamma-inactivated Ebola virus.

The label that is used to produce the labeled viruses of the present invention is preferably a fluorescent label. As taught herein, three means of labeling a virus with a fluorescent label have been developed. In a first aspect, the virus may be directly labeled by conjugating a fluorescent label to a virus, using chemical means known in the art, such as chemical linking. In a second aspect, the virus may be biotinylated and then labeled with a streptavadin:fluorescent label conjugate. Many medically important biotinylated viruses are also commercially available. In a third aspect, the virus may be labeled using fluorescently-labeled antibody that specifically recognizes and binds the virus. Such antibodies may be directly tagged by conjugating a fluorescent label to the antibody, using chemical means known in the art, such as chemical linking. Alternatively, the anti-virus antibodies may be biotinylated and then labeled with a streptavadin:fluorescent label conjugate. As with the virus, many biotinylated antibodies are commercially available. Suitable antibodies include the biotinylated anti-influenza A H1 specific antibody #1307 (ViroStat) and the biotinylated anti-influenza A H3 specific antibody #1317 (ViroStat).

In each of the embodiments of the invention, the virus may be a live virus, an inactivated virus, or an attenuated virus. When inactivated, the virus may be inactivated using BPL, or UV or gamma irradiation, or by any other chemical or physical method that preserves the ability of the virus to adhere specifically to the target cells.

In each of the embodiments of the invention, the population of target cells may be any cell line that can be bound by a virus, and/or into which a virus can penetrate. Suitable cell lines include mammalian cell lines, avian cell lines, amphibian cell lines, and other cell lines susceptible to viral attack. In one aspect, the population of target cells comprises a human cell line. In another aspect, the population of target cells comprises avian erythrocytes. In a further aspect, the population of target cells comprises a cell line selected from the group consisting of Madin-Darby canine kidney epithelial cells and Vero green monkey kidney epithelial cells.

In each of the embodiments of the invention, fluorescence may be measured through the use of a flow cytometer or a bead array reader. For example, a BioPlex-100, a BioPlex-200, a Luminex-100, or a Luminex-200 bead array reader may be used.

In each of the embodiments of the invention, the various steps in the disclosed methods can be conducted at different temperatures. For example, the step of incubating target cells with the labeled virus may conducted at temperatures conducive or inhibitory to endocytosis, such as at 37° C. or 4° C.

In each of the embodiments of the invention, the neutralizing activity of sera or an antibody is the blocking of entry of the labeled virus into the target cells.

In each of the embodiments of the invention, the fluorescent label may be phycoerythrin or allophycocyanin, or any other fluorescent molecule or molecular complex detectable via flow cytometry.

EXAMPLES

Materials: Suitable cells, viruses, biological materials, and equipment for conducting the examples described here include the following:

Cells: MDCK cell line (ATCC, #CCL-34); Vero cell line (ATCC); Turkey blood in citrate buffer, Rockland Immunochemicals.

Viruses: Solomon Islands H1N1 BPL-inactivated influenza virus; New Caledonia H1N1 BPL-inactivated influenza virus; Wisconsin H3N2 BPL-inactivated influenza virus. All viruses can be obtained as BPL-inactivated standards from the Centers for Disease Control, Atlanta, Ga.

Antibodies: Rabbit anti-human LDL, R & D Systems, #BAF2148; Goat anti-R-phycoerythrin, Rockland Immunochemicals #600-101-387; Goat anti-influenza A H1 IgG, ViroStat #1301; Goat anti-influenza A H1 IgG:biotin, ViroStat #1307; Goat anti-influenza A H3 IgG:biotin, ViroStat #1317; Goat anti-influenza A H1 IgG, Millipore #ab 1074.

Other components: Streptavidin-phycoerythrin, Millipore, #45-001; EZ-Link Sulfo-NHS-LC-biotin, Pierce #21335; Amine-reactive quenching dye QSY-9, Invitrogen #Q-20131; Human anti-influenza sera, from Florida Blood Bank, as used at VaxDesign for testing anti-influenza vaccination responses in the year 2008; Bovine serum albumin, heat-shock separated, low endotoxin, Sigma-Aldrich #A9430; Chicken egg albumin, grade V, Sigma-Aldrich #A5503; Human serum albumin, Sigma-Aldrich #A8763.

Equipment: Bead array readers: BioPlex-100 and BioPlex-200 (BioRad) were used effectively as simplified flow cytometers; flow cytometer: BD LSR II (BD Biosciences); orbital digital shakers: VWR #97006-944; 96-well U-shaped plates, clear polystyrene: VWR #29445-154.

Example 1

Influenza Virus as a Model for Developing the Neutralization Assay: Affinity Fluorescent Labeling BPL-inactivated influenza virus standards of various strains are readily available, for example, from the US Centers for Disease Control and Prevention (CDC). Solomon Islands H1N1, New Caledonia H1N1, and Wisconsin H3N2 strains containing ~$10^9$ viral particles/mL were used in most of the experiments, as examples.

Experiments were conducted with various labels, including direct biotinylation, quantum dots and fluorescent nanoparticles. Affinity labeling with biotinylated influenza A-specific antibodies with subsequent attachment of the fluorescent streptavidin-phycoerythrin (SA-PE) conjugate provided the brightest labeling of the influenza A virus. Direct biotinylation of the virus also provided an acceptable level of signal.

It was previously found that the goat polyclonal anti-influenza A H1 specific antibody #1301 (ViroStat) had a high affinity for H1N1 viruses, but low neutralizing capacity, when compared with the sera of influenza-vaccinated donors (data not shown). The biotinylated version of the same antibody (ViroStat #1307) was used for labeling Solomon Islands H1N1 and New Caledonia H1N1 viruses, while the biotinylated H3-specific antibody (ViroStat #1317) was used for labeling Wisconsin H3N2 virus. Labeling was performed at a low concentration of the antibodies, to prevent significant modification of the virus surface by the label.

An Example of Labeling Procedure

In embodiments of the present invention, an aliquot of the BPL-inactivated influenza virus, CDC standard, was typically diluted 1:10 in PBS containing 0.1% high-grade ovalbumin and 0.1% sodium azide ($NaN_3$). A biotinylated anti-influenza virus antibody, ViroStat #1307 or #1317 was added to the virus sample on ice, with stirring, to a final concentration 2.3 μg/mL. The sample was incubated overnight at 4° C. on a planetary shaker at 600 rpm. Afterwards, phycoerythrin-streptavidin conjugate (SA-PE) was added to the reaction mix on ice with constant stirring to a final dilution of 1:20 in the sample. After a further 24-h incubation at 4° C., the sample was diluted 1:10 in PBS containing 0.1% ovalbumin and 0.1% $NaN_3$, wrapped in aluminum foil, and stored in the refrigerator until further use. The preparation showed high stability for more than 3 months.

Labeling with a non-neutralizing antibody and SA-PE fluorescent conjugate proved to be facile and reliable, and provided the brightest fluorescence. Such labeling could be applied to inactivated and live viruses alike, with minimal effect from the contaminants in the virus culture.

From the relative sizes of the virus and the label, sparse surface labeling of the virus, even with a tag of high molecular weight, such as an antibody coupled with a SA-PE conjugate, was not expected to significantly alter adherence of the virus to target cells or to interfere with subsequent endocytosis of the virus by the target cells (FIG. 1).

Example 2

Assessing Replacement of the Affinity Label by Other Virus-Specific Antibodies An important question needed to be addressed before using the described affinity labeling in the neutralization experiments. Testing the neutralizing capacity of a test sera or other fluids requires incubating the labeled virus with a significant excess of other virus-specific antibodies in the tested sample, many of which may be cross-reactive with the viral epitopes recognized by the labeling antibody. It was therefore important to check whether other virus-specific antibodies would displace the labeling antibodies on the virus surface.

Figure 2:
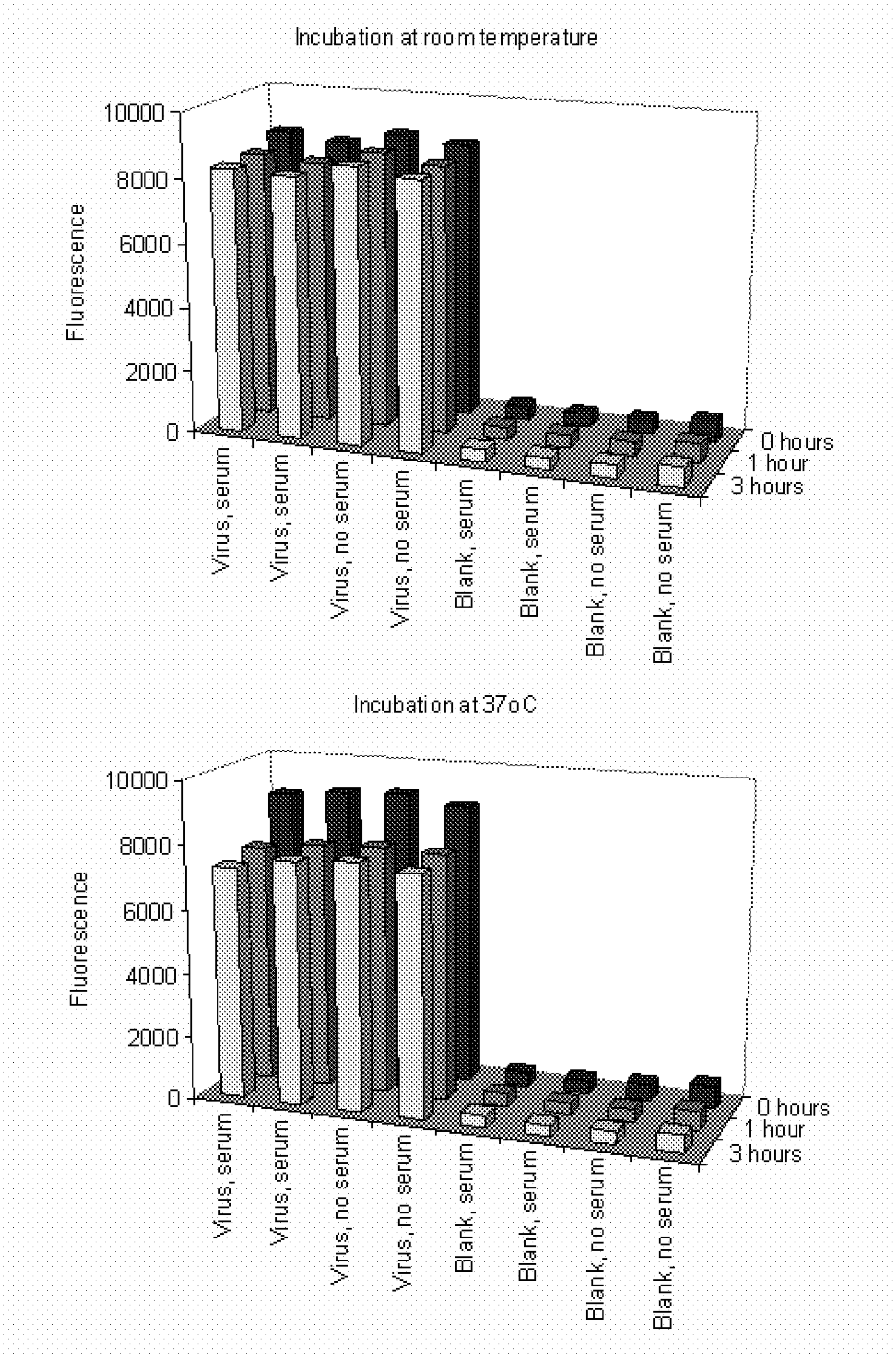
FIG. 2. Testing replacement of the affinity label by an anti-influenza serum: ELISA experiment. Solomon Islands H1N1 BPL-inactivated virus, CDC standard, was labeled in the ELISA wells with biotinylated anti-influenza A H1N1 antibody (ViroStat #1307), and tagged with SA-PE. An attempt was made to replace the label (SA-PE conjugated biotinylated ViroStat #1307) with an excess of anti-influenza serum from a vaccinated high-responding blood donor (#419).

Label replacement tests were performed at the same concentrations, volumes, temperatures, and times of incubation as the prospective neutralization assays (FIG. 2). In the first test, four wells of the ELISA plates were coated with inactivated Solomon Islands virus ("Virus"), and the other four wells were left blank ("Blank"), as negative controls. After blocking with 2% BSA and washing, the wells were then filled with the labeling biotinylated anti-influenza A antibody (ViroStat #1307), at 2 μg/mL. After incubation for 2 h at 4° C. and washing, the wells were filled with SA-PE conjugate, at 4 μg/mL. After the second 30-min incubation at 4° C. and washing, the wells were filled with PBS, and the plates were read in a Synergy HT plate reader (BioTek) in the phycoerythrin fluorescence channel ("0 hours"). Then, the wells were re-filled with either PBS ("no serum") or high-responder post-vaccination anti-influenza serum ("serum", #1250) at a dilution of 1/200 (estimated level of anti-influenza IgG, ~5-10 μg/mL). One of the plates was incubated at room temperature (FIG. 2A), and the other at 37° C. (FIG. 2B). After the first hour of incubation, the plates were washed, filled with PBS, and read again ("1 hour"), and then re-filled with the serum and PBS, incubated for 2 h, washed, and read again ("3 hours"). No label replacement was detected.

Figure 3:
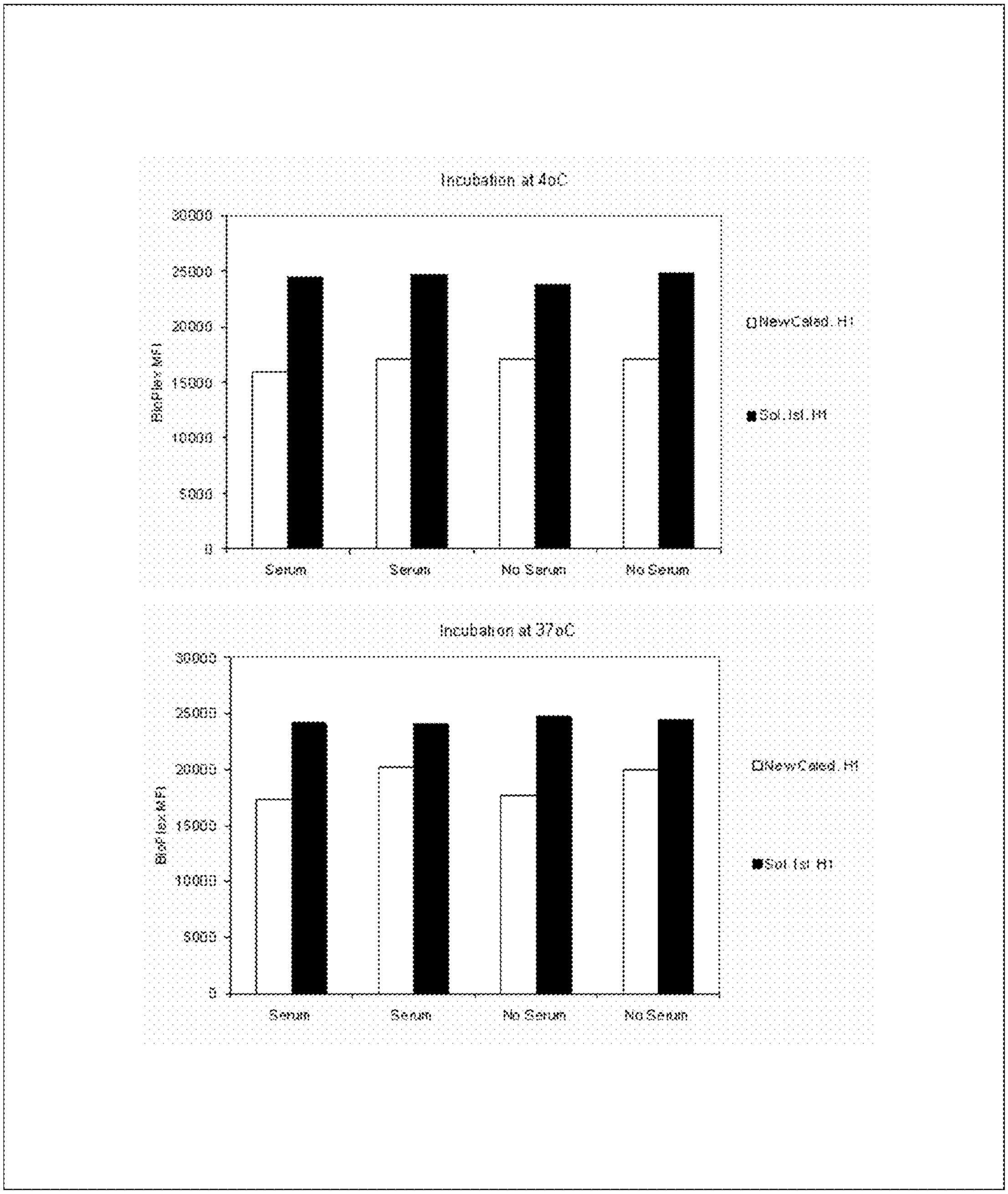
FIG. 3. Testing replacement of the affinity label by an anti-influenza serum: BioPlex experiment. Luminex beads coated with a recombinant H1 hemagglutinin from Solomon Islands H1N1 virus ("Sol. Isl. H1") or New Caledonia H1N1 virus ("New Caled. H1") were stained with the biotinylated ViroStat #1307 antibody coupled with the SA-PE conjugate and then incubated with an excess of anti-influenza serum from a vaccinated high-responding donor ("Serum") or PBS ("No Serum").

Another setup was performed using Luminex beads, chemically decorated with recombinant H1 hemagglutinins from Solomon Islands and New Caledonia H1N1 viruses, according to a modified Bio-Rad protocol (can be found at the Bio-Rad website www.bio-rad.com) (FIG. 3). The H1-coated beads were first incubated with the labeling biotinylated anti-influenza antibody (ViroStat #1307) in the same conditions as described above for the ELISA setup. After staining with SA-PE and washing, the beads were further incubated with either PBS ("No Serum"), or a high-responder anti-influenza serum ("No Serum"; #1250) at a dilution of 1:200. Then, the beads were washed and read in the BioPlex in the regular multiplex mode (FIG. 3). No replacement was detected.

The results shown in FIGS. 2 and 3 demonstrated that within the tested ranges of incubation times and temperatures, no replacement of the labeling antibodies took place. Insignificant decrease in the fluorescence signal observed for the ELISA samples after the first incubation, with or without the overlaying anti-influenza serum alike, was caused by washing out of a portion of loosely attached virus.

Some other tests of the replacement of the labeling antibody were performed; all of them showed negative results. Especially interesting was a test with the anti-influenza A H1 (ViroStat #1301), which is actually the same antibody as used for the labeling, although not biotinylated. In this experiment, the overlay of antibody #1301 contained 45 μg/mL of the antibody (i.e., 20 times higher than was used in the labeling with Ab #1307). Nonetheless, no replacement of the label was observed after a 1-h incubation at 37° C. (data not shown).

Example 3

Quenching of Surface-Bound Phycoerythrin Fluorescence

Monitoring fluorescently labeled virus engulfed by target cells inevitably requires subduing the fluorescence of surface-adherent virus. This can be done via extensive protease treatment of the cell surface, or (preferably) quenching of the surface-bound fluorescence using non- or low-fluorescence quenching agents. Trypan blue (TB) and crystal violet have been used successfully to quenching surface-bound fluorescein (Nichols et al. (1993) *Arch. Virol.* 130, 441; Collins & Buchholz (2005) *J. Virol. Meth.* 128, 192-197). It was found, however, that these non-specific quenchers were less effective in quenching the fluorescence of phycoerythrin (PE), likely because some of the phycobilin fluorescent clusters of PE are buried deep in the protein globule and inaccessible to the occasional contacts with quenching molecules.

To achieve more efficient quenching, an "addressed" affinity quencher was prepared, based on anti-PE antibodies. Specifically, fluorescence quenching dyes QSY-9 and QSY-21 (Invitrogen) were linked to a goat anti-R-phycoerythrin antibody (Rockland Immunochemicals #600-101-387). Such an affinity quencher binds specifically to the PE tags labeling the virus. The quenching occurs through Forster Resonance Energy Transfer (FRET) between the adjacent QSY molecules and phycobilin fluorescent clusters of PE rather than via direct contacts of the fluorochrome with a non-specific quencher.

Figure 4:
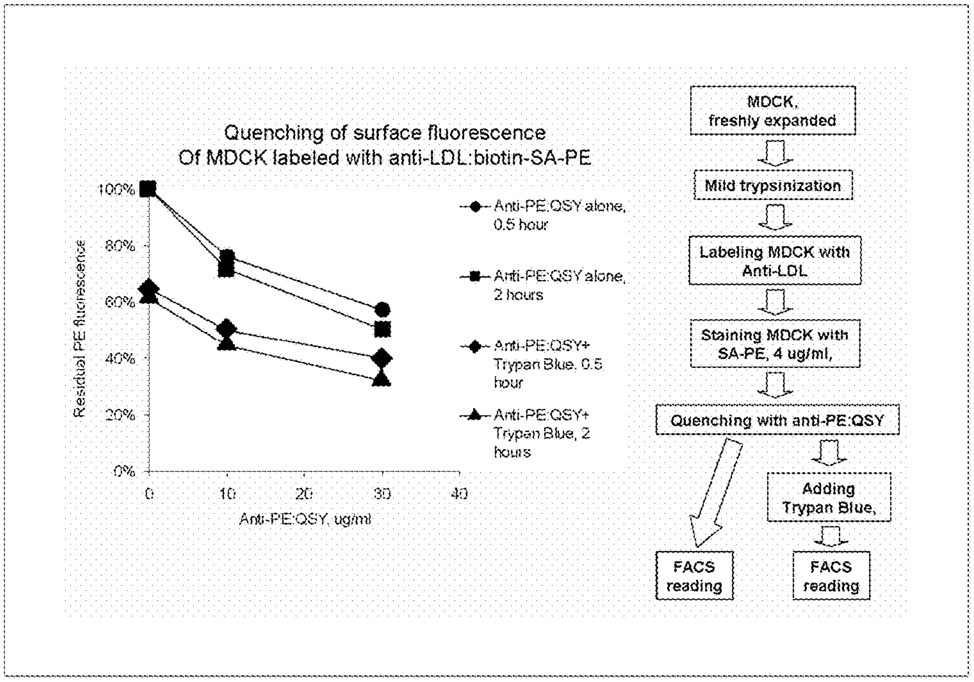
FIG. 4. Quenching of phycoerythrin fluorescence using an anti-phycoerythrin antibody coupled with QSY quencher. MDCK (Madin-Darby canine kidney) cells were labeled using a biotinylated anti-LDL antibody, coupled with the SA-PE conjugate. The cells were incubated at 4° C. with an anti-PE (phycoerythrin) antibody tagged with QSY-9 fluorescence quenching dye. Trypan blue was added (400 μg/mL) to achieve additional non-specific quenching.

To assess the quenching protocol, an interim model was used: MDCK cells tagged with biotinylated anti-LDL antibodies and stained with SA-PE conjugate. This model mimicked the same MDCK cells bearing surface-attached PE-labeled virus. The anti-PE quenching QSY-9-linked antibody was added to the labeled cells at 10-30 μg/mL, and the cells were incubated at 4° C. Combined with 400 μg/mL trypan blue, anti-PE quenchers subdued 65% of the PE fluorescence of the labeled cells (FIG. 4).

Example 4

Use of a BioPlex Bead Array Reader as a Simplified Flow Cytometer

Upon incubation of fluorescently labeled virus with target cells, the latter can be read in a flow cytometry device to detect incorporated virus. Modern flow cytometers are versatile and expensive machines able to monitor multi-colored labels. This powerful capacity may be excessive and too expensive for microneutralization assays, which are intended to be high-throughput and routine procedures.

In this example, we used a BioPlex-100 bead array reader for reading PE fluorescence of the virus engulfed by the target cells (fmNt mode) or attached to the surface of the target cells (fADI mode). The BioPlex reader and its accessories are significantly less expensive than a flow cytometer, and the reader requires less maintenance. Literature regarding BioPlex readers may be found at the website beginning with "www." and ending with "bio-rad.com/cmc_upload/Literature/54967/Bulletin_2890.pdf."

The BioPlex reader is designed for immunosorption experiments, where it reads fluorescence from phycoerythrin-conjugated anti-analyte antibodies attached to the 5.6-μm plastic beads coated with analyte-capturing antibodies. The beads flow through the capillary fluorescence chamber.

In general, this scheme is similar to a most basic flow cytometry experiment, where calibrated micro beads play the role of the cells. However, there is an important difference. The beads used in the BioPlex are coded via their intrinsic red/infrared fluorescence in such a way that the ratio of the red and infrared components determines the code number of the bead. This allows discrimination of signals from a multitude (currently, up to 200) of beads with different codes, which provides for the exceptional multiplexing capacity of the BioPlex (BioRad Bulletin 2890).

Figure 5:
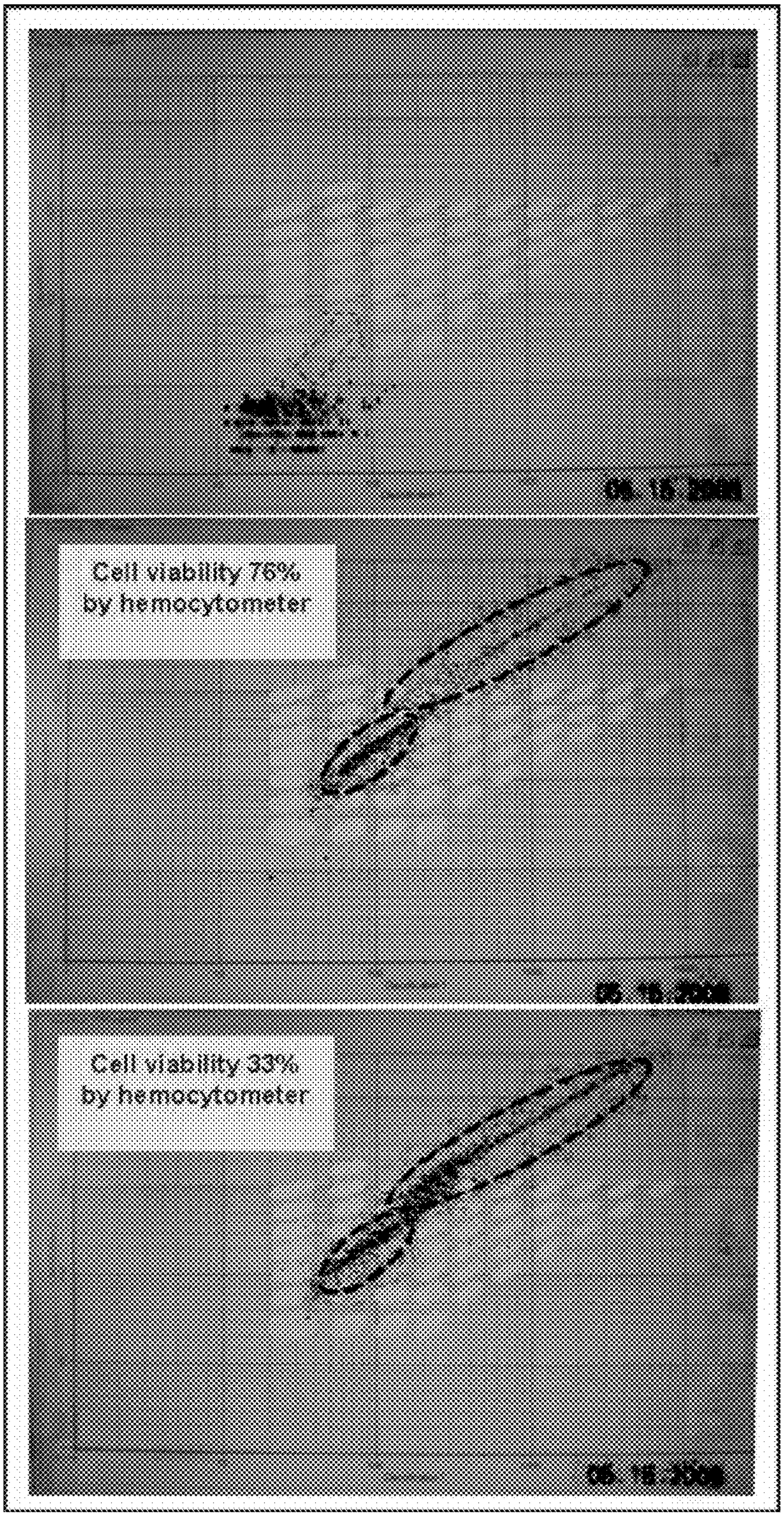
FIG. 5. Staining cells with trypan blue made them 'readable' in the BioPlex bead array reader. Depicted is the two-dimensional classification panel of the BioPlex-100, the y-axis representing infrared fluorescence, and the x-axis, red fluorescence. Multiple pale ovals in the middle of the map are classification regions designated for the appropriately coded beads. Upper panel: Unstained MDCK cells were registered by the BioPlex, but their fluorescence was not read, because they were not classified as legitimate objects. Middle and Lower panels: Cells were stained with 500 μg/mL trypan blue. Their images shifted upward and rightward in the classification panel. Many cells were classified as legitimate objects, and their fluorescence was measured by the BioPlex reader. The lower, smaller circle on each panel encompasses normal healthy cells; the upper, larger circle on each panel encompasses damaged and dying cells.

As a result of this design, fluorescence signals from ordinary cells cannot be measured on the BioPlex directly, because the cells do not produce a recognizable red/infrared fluorescence code. However, additional staining of the cells with an appropriate red/infrared fluorescent dye(s) can overcome this hurdle. We found that common staining dyes, such as trypan blue (TB) and crystal violet (CV), when used at low concentrations, were able to 'code' target cells such as MDCK and Vero mammalian kidney epithelial cultures, or avian erythrocytes. TB, a dark blue staining dye, is commonly used in the dye exclusion method, where apoptotic cells with damaged surface membranes take up the dye, turning dark blue, while normal cells do not. However, it is also true that normal cells become weakly stained with TB on their surface, which is normally not observable by light microscopy as used in the dye exclusion assays. TB possesses a weak red/infrared fluorescence, and surface staining of normal and healthy cells with TB occurs sufficient for their recognition by the classification system of the BioPlex reader as readable objects. Damaged and dying cells carry higher loads of TB, which results in stronger red/infrared fluorescence and, accordingly, different positioning of the cells in the classification panel of the BioPlex. This allows effective discrimination between normal and abnormal cells in these flow experiments (FIG. 5).

It was found that staining cells with TB usually produced certain background fluorescence in the detecting channel of the BioPlex reader, which is tuned to the orange fluorescence of the PE fluorochrome. However, this background was normally significantly lower than the signal from the PE tag of the labeled viruses in and on the target cells, and therefore the background and the informative signal from the SA-PE tag could be readily discriminated (FIGS. 5 and 6).

Example 5

Figure 6:
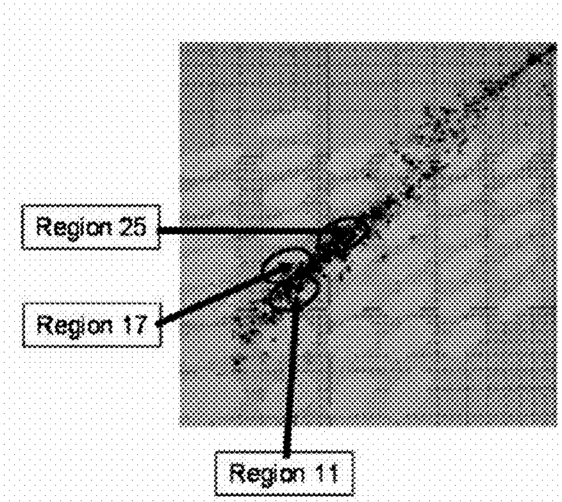
FIG. 6. Comparing fluorescence of the labeled cells measured in the flow cytometer and the BioPlex bead array reader. Regions 11, 17, and 25 of the BioPlex classification panel (upper left) were used to calculate the pooled average mean fluorescence index (MFI) of the labeled cells read in the BioPlex. The table shows numbers of cells registered in each of the three regions and the mean fluorescence index (MFI) calculated.
Figure 6:
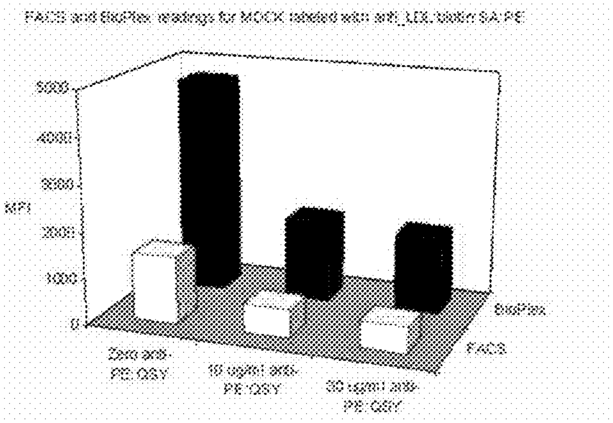

Comparison of Results Obtained in the Flow Cytometer and the BioPlex Bead Array Reader To demonstrate the capacity of the BioPlex to function as a simplified flow cytometer, an experiment on quenching of the PE fluorescence of surface-labeled MDCK cells was performed using a BD LSR II flow cytometer (PE channel) and a BioPlex-100 bead array reader in parallel (FIG. 6).

The BioPlex results were found to be fully consistent with the flow cytometer data. The efficiency of cell reading in the BioPlex was about 35-40%. The BioPlex also showed a capacity to produce reliable results from a limited number of the registered cells as compared to tens of thousands cells normally required for the experiments on a flow cytometer. In the conditions of the experiment, reading regions #11, #17 and #25 were selected for calculating the pool averaged mean fluorescence index (MFI), which represented the averaged fluorescence signal from the target cells.

Example 6

BioPlex-Based fmNt Assay

Figure 7:
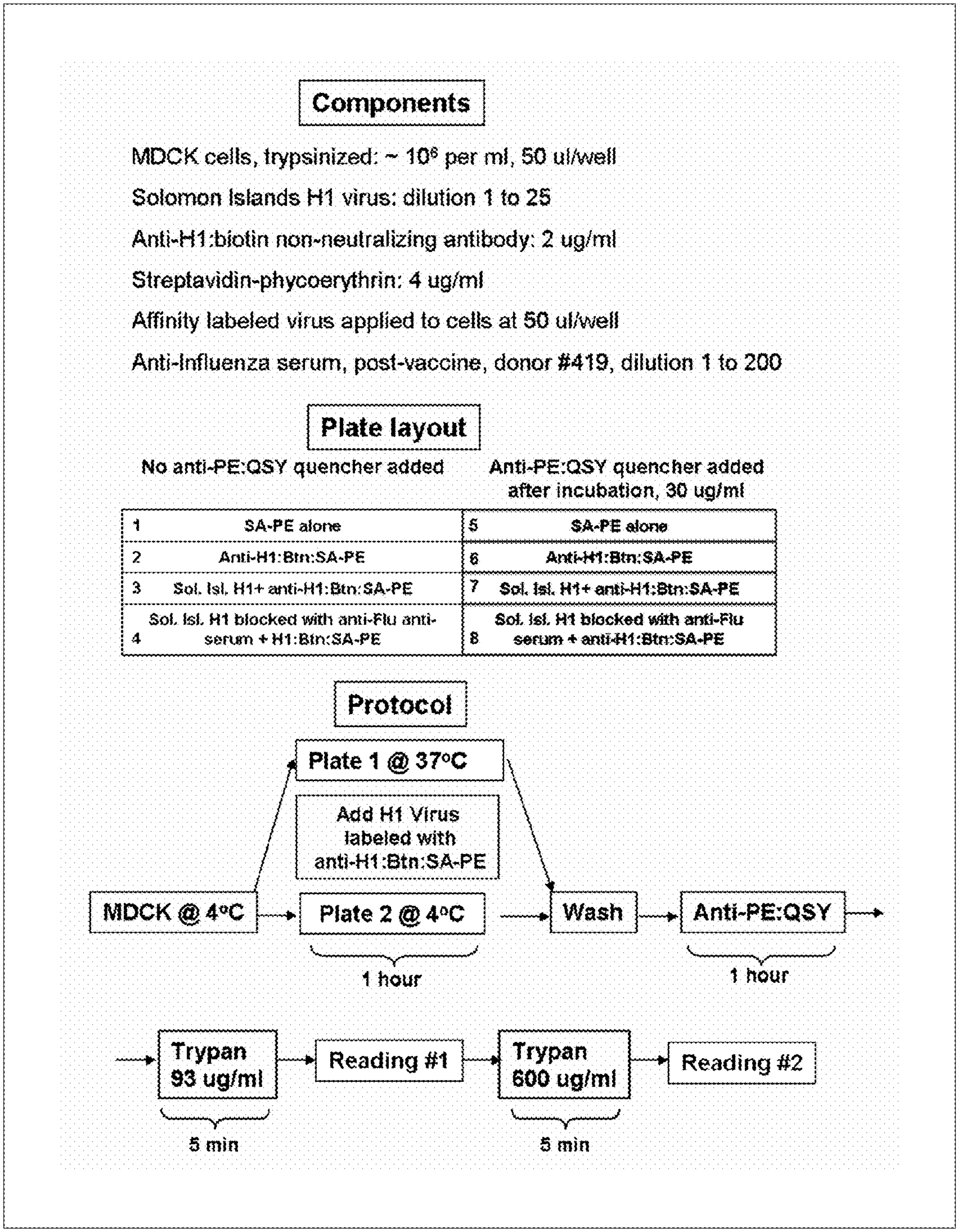
FIG. 7. Layout and the protocol for the BioPlex fmNt experiment with BPL-inactivated Solomon Islands H1N1 virus and MDCK target cells. Two identical plates were prepared in which the labeled virus or the components of the labeling without virus was incubated with MDCK cells at 4° C. or at 37° C. In each plate, the left part of the layout was prepared without the PE-specific quencher, and the right parts with the PE-specific quencher. The concentrations/dilutions of the components indicated are prior to mixing in the wells. The detailed description of the procedure is in the text.

Two identical 96-well format round-bottom plates were prepared as shown in the layout table in FIG. 7. In these plates, MDCK target cells were mixed with influenza H1N1 Solomon Islands BPL-inactivated virus, affinity-labeled using anti-influenza A biotinylated antibody and SA-PE conjugate. The labeled virus was, or was not pre-incubated with high-titer anti-influenza human serum. One of the plates was further incubated at 37° C., where endocytosis of the virus is efficient. Another plate was incubated at 4° C., where endocytosis is strongly subdued. After the incubation, the plates were centrifuged (400 g; 4° C.) and washed with cold PBS solution twice. Then the cells in half of the wells in each plate were re-suspended with 0.1% BSA in cold PBS, while the cells in the other half were re-suspended in the same solution containing 30 μg/mL anti-PE:QSY quencher, and the plates were incubated for another 1 h at 4° C. Then, 70 μL of PBS containing 160 μg/mL trypan blue was added to each well, the plates were incubated for min at room temperature and read in the BioPlex reader. After that, another portion of 30 μL of concentrated TB solution was added, to a final concentration of 600 μg/mL, and the plates were read again (see FIG. 7 for the protocol and FIGS. 8 and 9 for the results). The resultant mean fluorescence index (MFI) numbers were calculated using the same reading regions #11, #17 and #25, and the same calculation procedure as described in Example 5.

Figure 8:
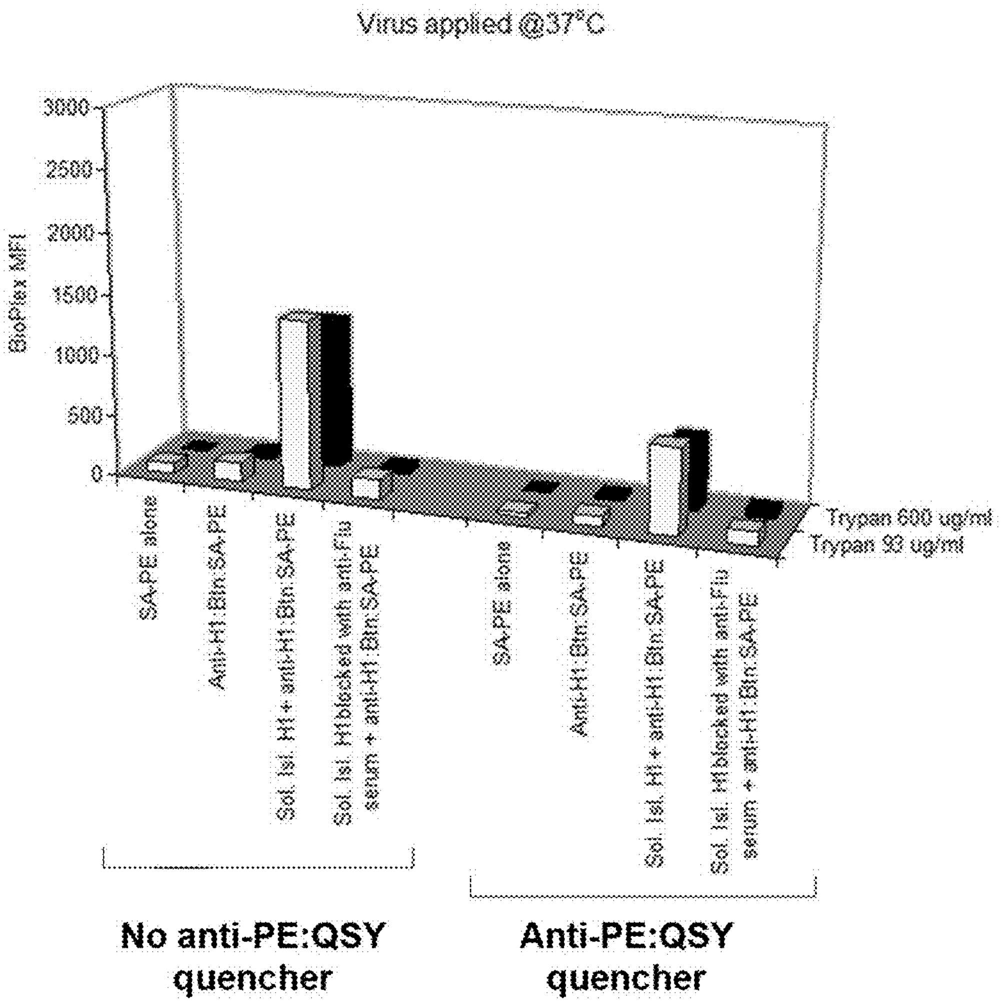
FIG. 8. Results of the proof-of-concept fmNt experiment performed at 37° C. Components of the label without virus did not bring fluorescence to the target cells ("SA-PE alone" and "Anti-H1:Btn:SA-PE"). Together with the virus (H1N1 Solomon Islands, BPL-inactivated), the fluorescence of the cells increased dramatically ("Sol. Isl. H1+anti-H1:Btn:SA-PE"). Pre-incubation of the virus with anti-influenza serum strongly reduced the fluorescence ("Sol. Isl. H1 blocked with anti-Flu serum+anti-H1:Btn:SA-PE"). PE-specific (anti-PE: QSY-9) and non-specific (TB; trypan blue) fluorescence quenchers reduced the fluorescence from surface-bound virus.
Figure 9:
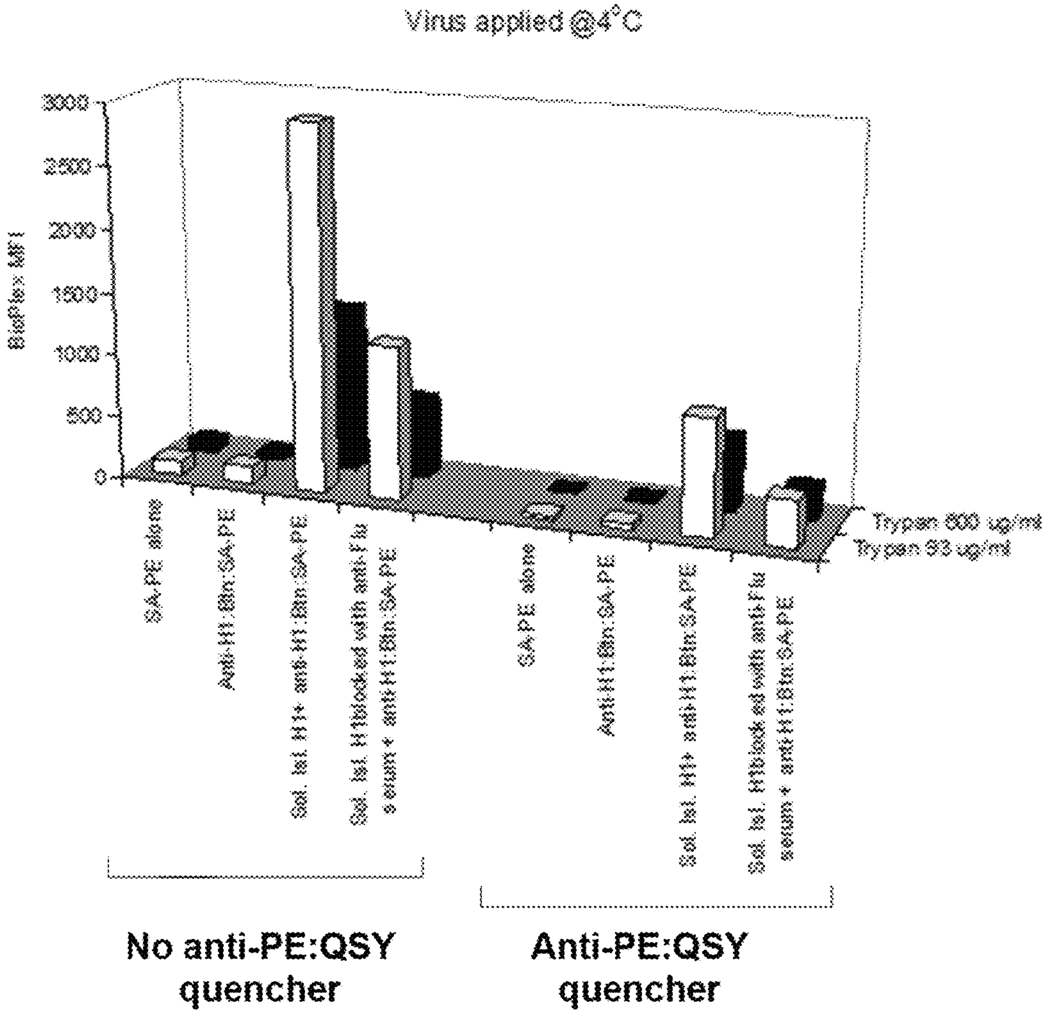
FIG. 9. Results of the proof-of-concept fmNt experiment performed at 4° C. Fluorescent signals of the target cells as well as the relative effects of the fluorescence quenchers increased, because at the lower temperature the endocytosis is subdued, and most of the viruses remained attached to the surface of the cells.

The results of the BP-fmNt experiment shown in FIGS. 8 and 9 demonstrate important features of the fmNt assays of the present invention. Without virus, neither SA-PE conjugate alone, nor its complex with biotinylated anti-influenza antibody produced any significant fluorescence in the target cells, showing only a low non-specific background coming from TB staining of the target cells. In contrast, influenza virus labeled with the anti-influenza:biotin:SA-PE complex and applied to the target cells provided bright fluorescence. This demonstrated the efficient interaction of the target cells with the labeled virus. Pre-incubation of the labeled virus with human anti-influenza serum significantly reduced the fluorescence of the target cells, as it should be expected in the neutralization experiment. This reduction was more dramatic for the samples incubated at 37° C. versus 4° C. The latter effect likely reflected the relatively smaller portion of the labeled virus bound to the surface of the target cells at 37° C., compared with engulfed virus. The quenching effect of both the PE-specific quenching antibodies and nonspecific TB was stronger for samples incubated at 4° C. versus 37° C. This likely reflected the higher share of the surface-bound virus towards the engulfed virus, as it should be expected at 4° C., where endocytosis is effectively subdued.

In summary, the BP-fmNt assay described in this example demonstrated crucially important elements of a microneutralization experiment: (i) selective binding of the labeled virus by the target cells, but not of the bare label; (ii) efficient quenching of the surface bound fluorescence, and (iii) efficient blocking of virus attachment and engulfment by anti-virus serum.

Example 7

Figure 10:
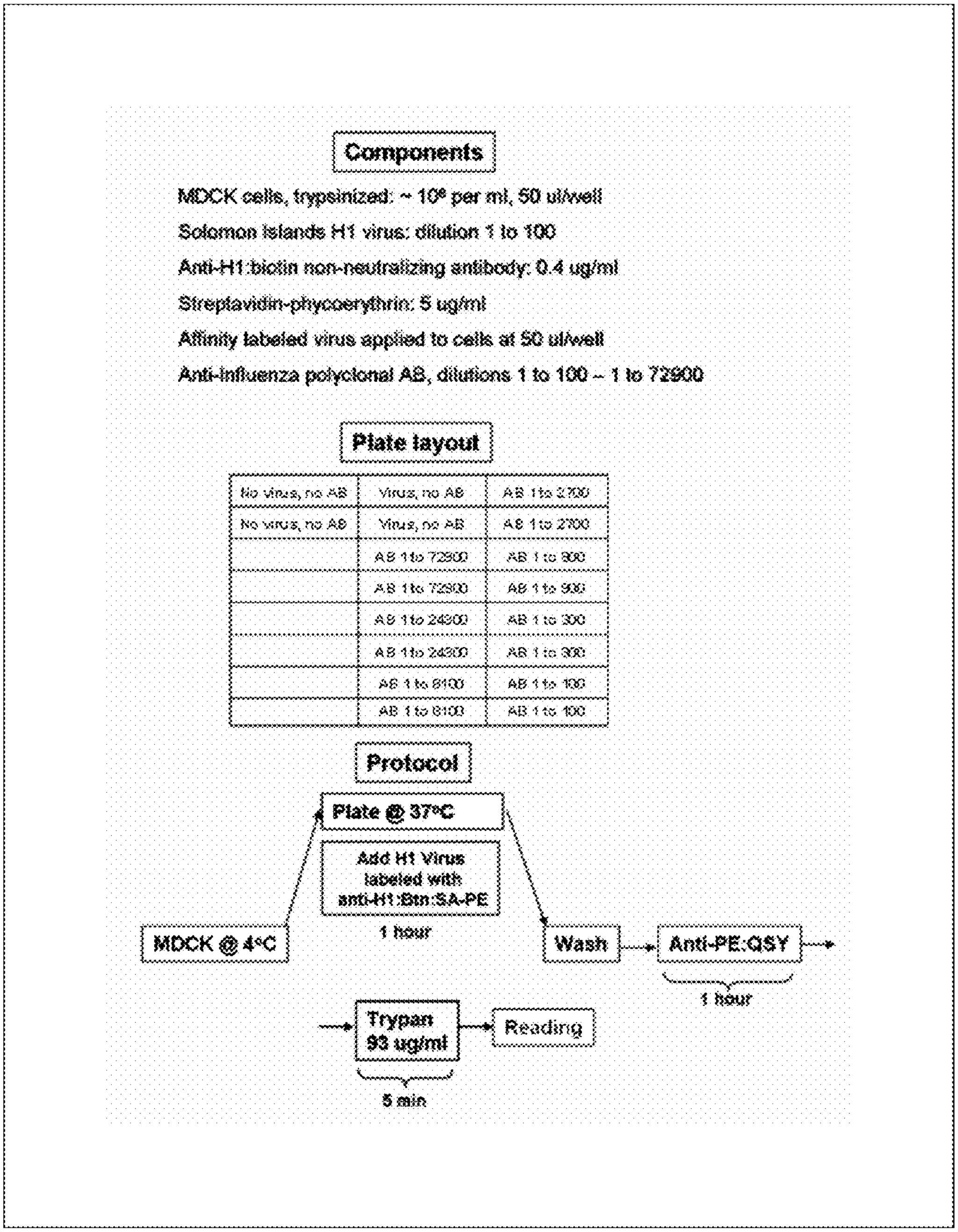
FIG. 10. Components, layout, and protocol for measuring neutralizing capacity of commercial anti-influenza A antibodies.
Figure 11:
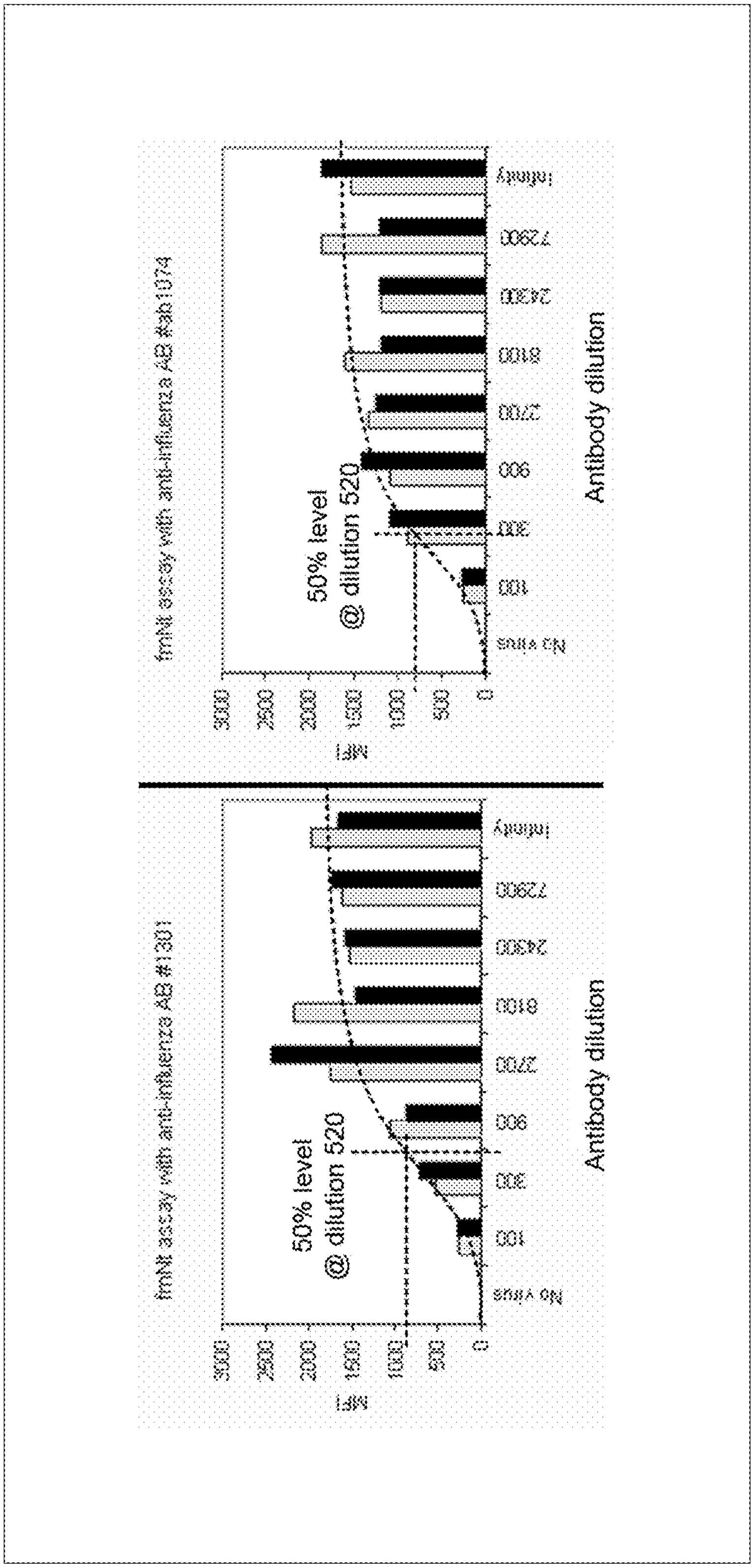
FIG. 11. Neutralizing capacity of commercial anti-influenza antibodies, as determined using the fmNt method. Dashed lines show the fitting to the theoretical titration curves and the 50% cut-off titers. The titers show moderate-to-low neutralizing capacity for both ViroStat and Millipore specimens.

Determination of the Neutralizing Titer of Commercial Anti-Influenza Polyclonal Antibodies Using the fmNt Technique The neutralizing capacity of commercial anti-influenza A polyclonal antibodies was determined using the fmNt protocol described in Example 6, with the following minor modifications. The concentration of the labeled virus was reduced; the second reading with an increased concentration of TB was eliminated, and dilutions of the tested antibodies varied from 100 to 72,900 (FIGS. 10, 11). All the samples were assayed in duplicates. The dilutions corresponding to the 50% cut-off of the fluorescence, chosen as the neutralizing titers, were determined by the least-square best fit to the theoretical titration curve. The fmNt titers, 520 and 350, obtained for the commercial polyclonal antibodies, ViroStat #1031 and Millipore # ab 1074, respectively (FIG. 11), corresponded to concentrations of the IgG of 70-90 nM, demonstrating that these antibodies were weak-to-moderate neutralizers.

Example 8

Determination of the fmNt Titers of Human Sera

Figure 12:
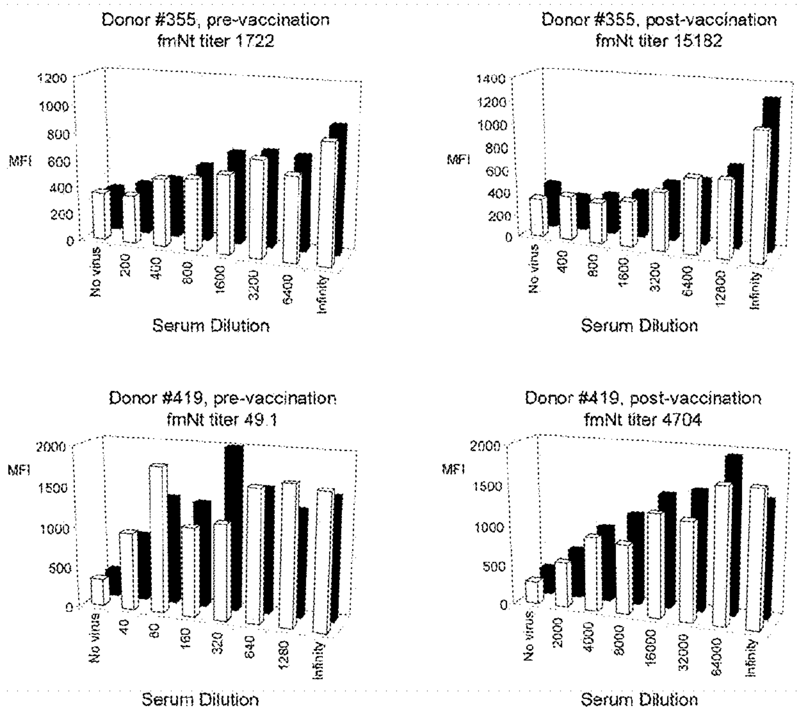
FIG. 12. Neutralizing capacity of human anti-influenza sera, as determined using the fmNt method. The fmNt titers shift sharply upward after vaccination thus demonstrating a strong neutralizing capacity of the post-vaccination sera.

The neutralizing capacity of human anti-influenza sera was assessed using a scheme similar to that used for the commercial anti-influenza antibodies described in Example 7. Samples of human sera taken before and after vaccination from donors #355 and #419 (high-level responders, as was found in earlier screening of the sera samples in the standard HAI assays) were pre-diluted roughly in accordance with their expected neutralizing capacity, and then serially diluted as shown in FIG. 12, which displays the results of the assay. The fmNt experiments showed a significant increase of the neutralizing titers of the post-vaccination versus pre-vaccination sera. The fmNt titers demonstrated that the neutralizing capacity of the anti-influenza antibodies of the post-vaccination human sera was ~100 times higher than for the commercial antibodies, taking into consideration an average IgG level ~10-15 mg/mL in the normalized human sera, ~10% of which can be ascribed to an anti-influenza immune response. For example, the fmNt titer for the post-vaccination serum #355 was determined to be ~15000, corresponding to a concentration of neutralizing IgG of ~0.7 nM (compare with the results for the anti-influenza A antibodies in Example 7, FIG. 11).

Example 9

Comparison of Neutralizing Titers Found in the fmNt Assays with BPL-Inactivated Virus with Approved MN Protocols Using Live Virus Comparative microneutralization experiments were performed on a panel of 16 sera from eight donors vaccinated in the 2007/2008 flu season. The sera were selected from a whole panel of 36 sera, in such a way that their HAI titers would cover a wide range, from the lowest titers for the pre-vaccination sera to the highest titers of high-responding post-vaccination sera.

The fluorescent microneutralization (fmNt) experiments using the BPL-inactivated Solomon Islands H1N1 virus were performed in March-April 2009.

Solomon Islands H1N1 virus was expanded on the MDCK culture, and microneutralization (MN) assays using the immunosorption enzyme linked protocol (CDC protocol; Rowe et al. (1999) *J. Clin. Microbiol.* 37, 937-943) and direct MN protocol based on hemagglutination (HA) measurements of the expanding virus (WHO protocol described in the "WHO Manual on Animal Influenza Diagnosis and Surveillance," (WHO/CDS/CSR/NCS/2002.5 Rev. 1) using live Solomon Islands H1N1 virus were performed in May-August 2009.

Figure 13:
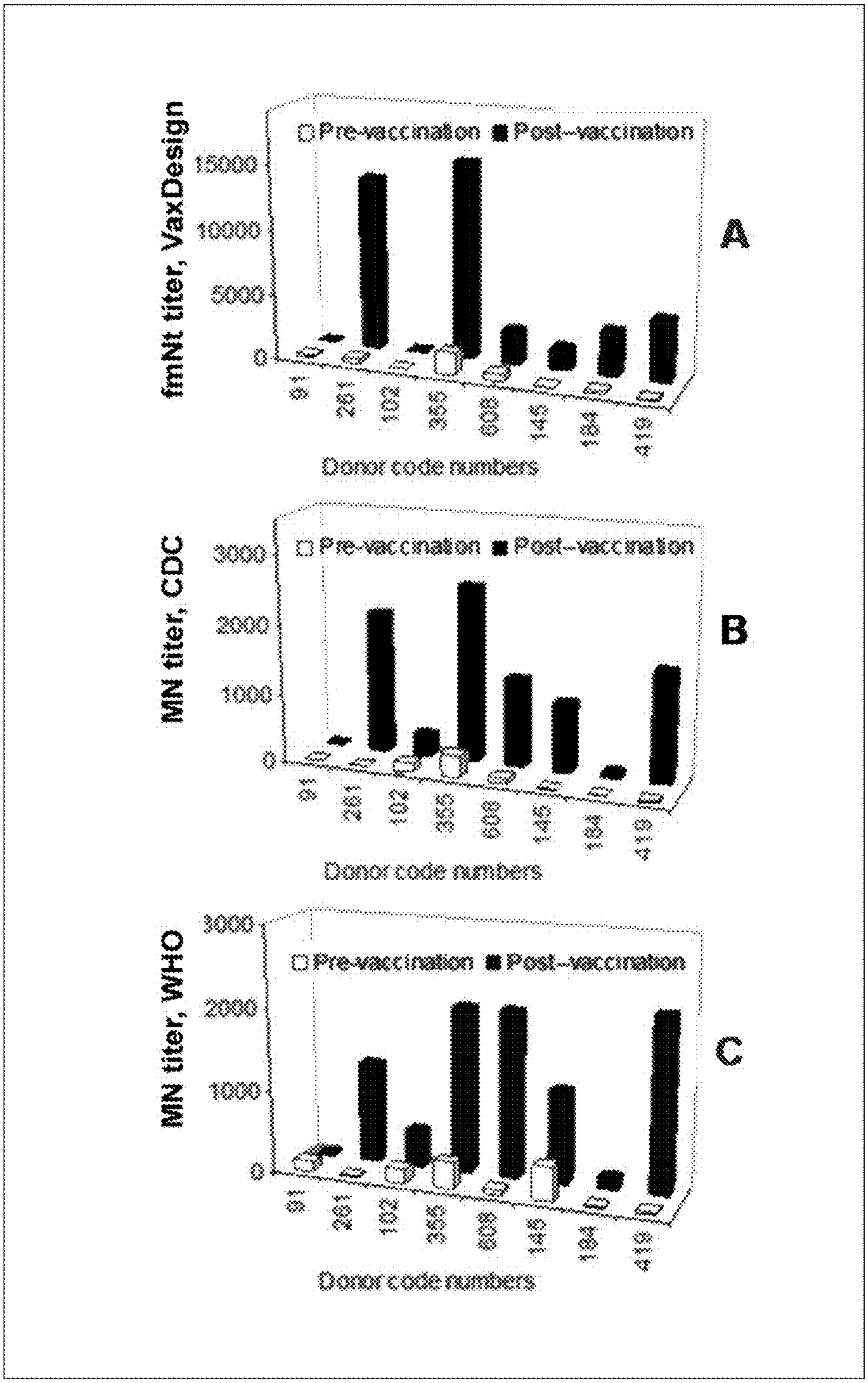
FIG. 13. Comparison of the neutralizing titers of pre- and post-vaccination sera from donors immunized against seasonal influenza obtained using the VaxDesign fmNt protocol (FIG. 13A) and CDC (FIG. 13B) and WHO (FIG. 13C) MN protocols. The data from the fmNt experiments with BPL-inactivated Solomon Islands virus demonstrated a strong correlation with the experiments using live virus according to the standard MN protocols practiced by CDC and WHO. The fmNt experiment demonstrated the superior sensitivity of the assay of the present invention.

The results shown in FIG. 13 demonstrate remarkable parallelism in the neutralization titers obtained for the inactivated virus using the fmNt technique, and for the live virus using the standard CDC and WHO protocols. This observation was corroborated by significant cross-correlation coefficients for the inactivated virus and the live virus results, shown in Table 1.

TABLE 1

| | fmNt | FIA-CDC | MN-WHO |
|---|---|---|---|
| fmNt | X | 0.901 | 0.661 |
| FIA-CDC | X | X | 0.904 |
| MN-WHO | X | X | X |

Additionally, the fmNt assay demonstrated sensitivity to the neutralizing sera 3-5 times higher than the FIA and the MN protocols, as can be seen by comparing the corresponding MN and fmNt titers for the different assays in FIG. 13.

Example 10

Fluorescent Adherence Inhibition Assay (fADI)

Adherence of the virus to the surface of the target cells is normally considered an obstructing factor in fluorescent microneutralization, which should be minimized or eliminated. However, surface adherence of the virus is a necessary step for infection, preceding engulfment by the target cell. Logically, such a phenomenon has no less relevance to infectivity of the virus than agglutination of erythrocytes employed as signaling factor in the HA and HAI assays. It is reasonable to expect that virus-specific antibodies will be able to block surface adherence with an efficiency at least comparable with that demonstrated in blocking the penetration of the virus into the target cells.

Figure 14:
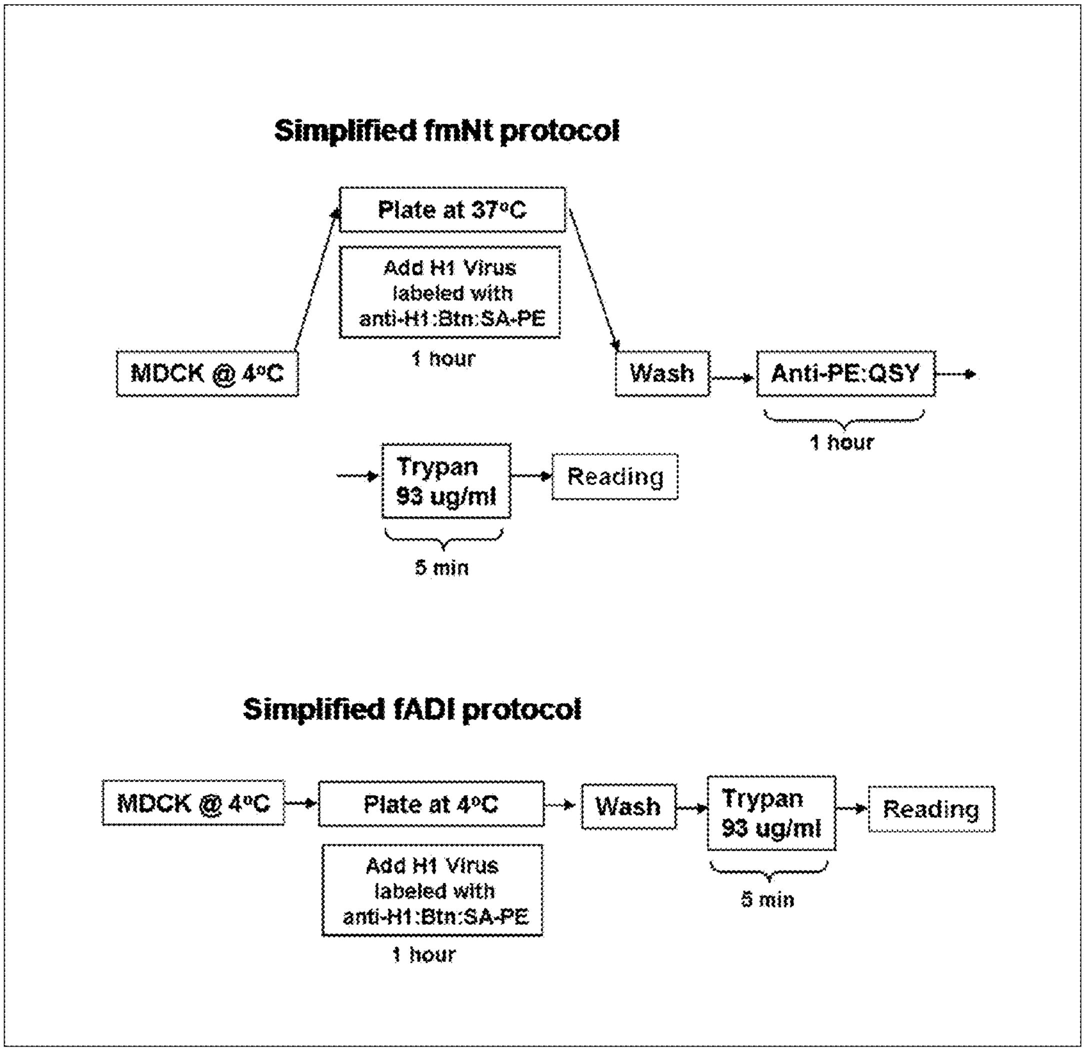
FIG. 14. Comparison of fmNt (FIG. 14A) and fADI (FIG. 14B) protocols. The fADI protocol required almost 50% less incubation time and did not use an anti-PE surface quencher. Affinity labeled Solomon Islands H1N1 BPL-inactivated virus; MDCK target cells.
Figure 15:
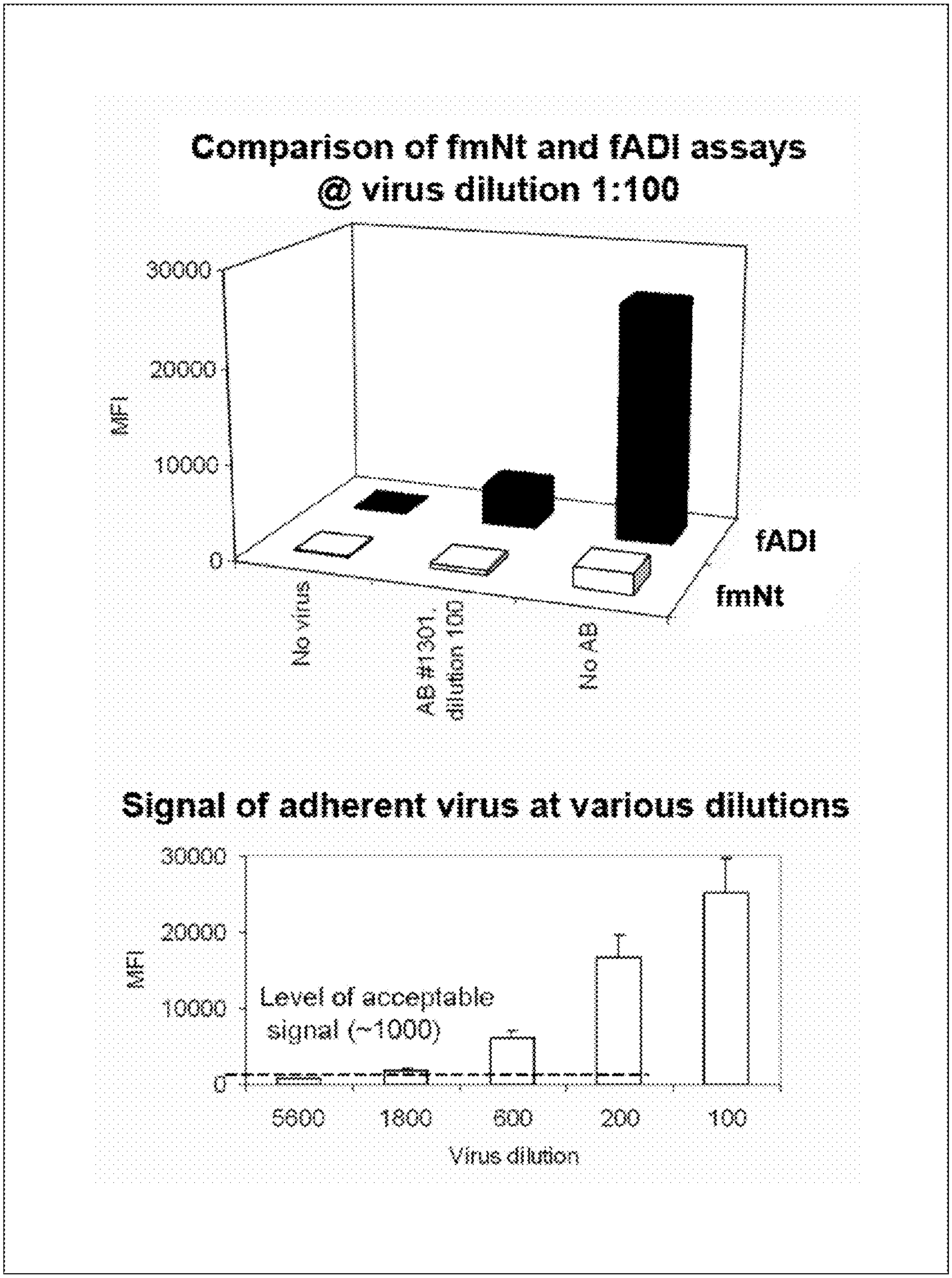
FIG. 15. Comparison of fmNt and fADI measurements.
Figure 16:
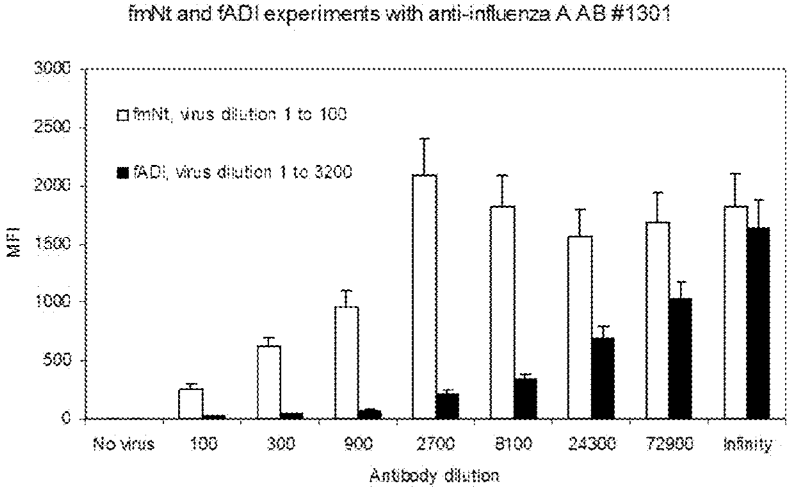
FIG. 16. Comparison of fmNt and fADI titers for a commercial anti-influenza A antibody. Upper insert: fmNt and fADI titrating neutralizing capacity of anti-influenza A, ViroStat #1301. Lower insert: Juxtaposition of neutralizing titers of the ViroStat #1301 antibody and the virus dilutions used in the fmNt and fADI experiments. Higher sensitivity of the fADI method corresponds to the higher dilution of the virus used in the experiment. Affinity-labeled Solomon Islands H1N1 BPL-inactivated virus; MDCK target cells.

The well-known and widely used hemagglutination inhibition assay (HAI) actually explores blocking of the attachment of the virus to the surface of the target cells (erythrocytes). The importance of the HAI and continuing interest in using it supports the idea that monitoring of the inhibition of adherence of the virus to the target cells by a virus-specific antibody, in general, can provide data of significant interest. Further, the protocol for a fluorescent adherence inhibition assay (fADI) can be simpler, shorter, and less material- and time-consuming than a fmNt experiment, because the fADI does not require application of surface fluorescence quenchers and an additional incubation (FIG. 14). The fADI assay measures the capacity of virus-specific antibody or sera to block adherence of the virus to the target cell. Importantly, the fluorescent fADI experiment can provide a stronger fluorescence signal from the target cells (FIG. 15). This, in its turn, can allow working at lower concentrations of the labeled virus, thus providing higher sensitivity of the assay versus the fmNt, as is shown in the titration of a commercial anti-influenza A antibody (ViroStat #1301) using fmNt and fADI methods, displayed in FIG. 16. The dilutions of the affinity-labeled influenza virus used in these assays were 100 and 3200, respectively, and the 50% blocking titers for the antibody were found as 520±180 and 32700±18500 (i.e., roughly proportional to the virus dilution).

Example 11 fADI Experiments Using Turkey Erythrocytes and New Caledonia H1N1 Influenza Virus The capacity of influenza viruses to attach to erythrocytes of different species (e.g., human, guinea pig, swine, chicken, turkey) is widely used in the routine titration of virus cultures in the HA technique, and in testing the neutralizing capacity of sera with HAI assays. In these methods, erythrocytes used at relatively high concentrations (~1% HCT) are agglutinated by virus particles in a translucent three-dimensional gel matrix. At lower concentrations, spatial agglutination is not possible, although virus attachment remains strong. Adherence of the fluorescently labeled virus to erythrocytes can be detected in a flow cytometry experiment analogous to that described above for MDCK target cells.

For such experiments, large and heavy avian erythrocytes were found to be preferable to mammalian erythrocytes, because the BioPlex bead array reader and the flow cytometer better detected the former.

Fresh samples of turkey blood balanced with citrate buffer were washed three times in PBS (at 400 g), and the upper layer of the pellet containing lymphocytes was discarded. The washed erythrocytes were diluted in 1% human serum albumin (HSA) in PBS to the level of 0.03% HCT.

Figure 17:
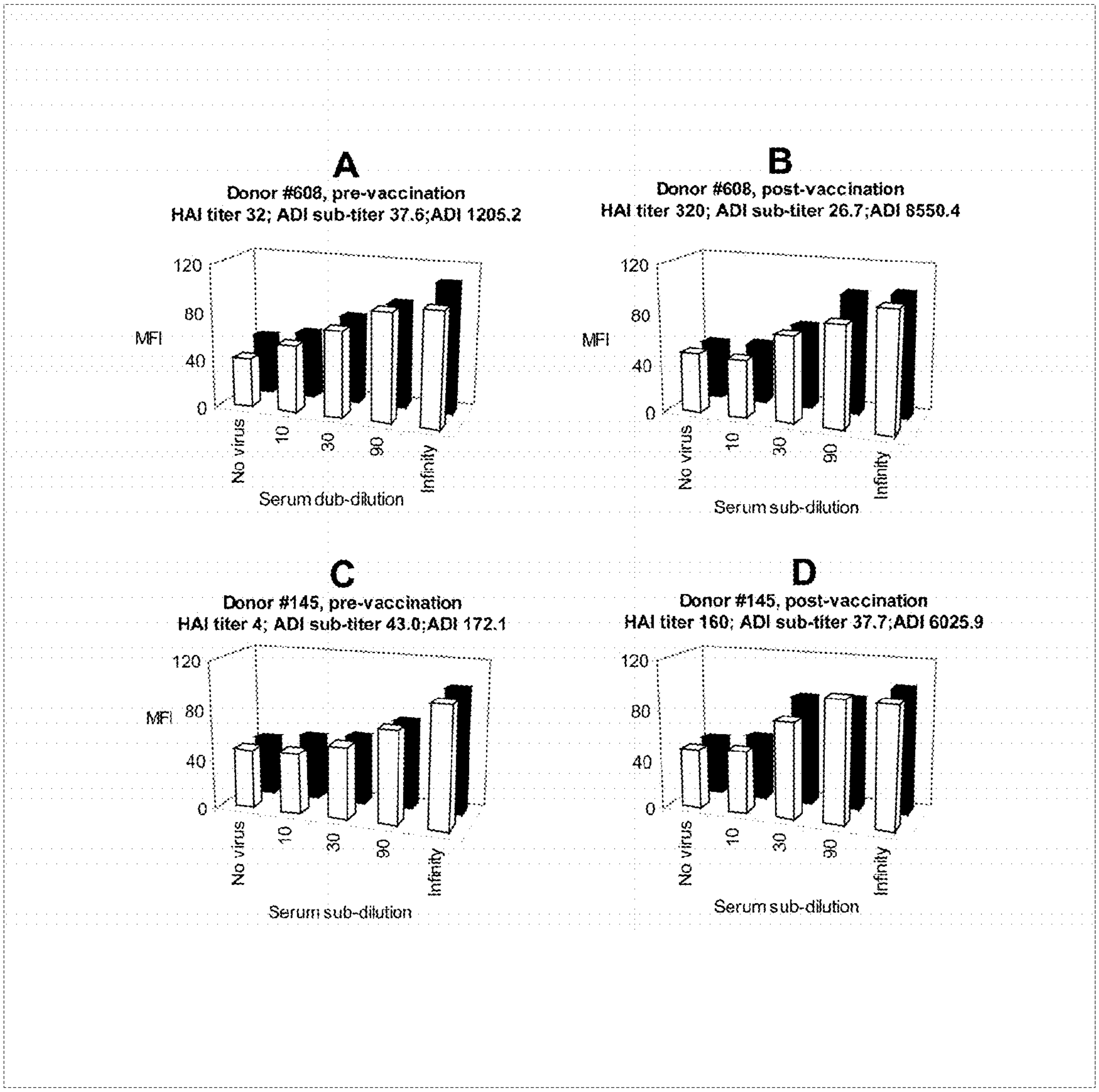
FIG. 17. Neutralizing capacity of human anti-influenza sera towards H1N1 virus, as determined using the fADI method and turkey erythrocytes as targets. Sera samples were pre-diluted according to their pre-determined HAI titers. The fADI titers shift upward after vaccination.

As an example, New Caledonia H1N1 BPL-inactivated virus was chosen for these experiments (Solomon Islands H1N1 strain also showed acceptable results; data not shown). New Caledonia H1N1 BPL-inactivated virus, affinity labeled with the same biotinylated anti-H1 ViroStat antibody #1307, as described above for Solomon Islands H1N1, was finally diluted 3200-fold in 1% HSA in PBS. Samples of donor sera were diluted in 1% HSA/PBS to the levels of their previously determined HAI titers (e.g., the sample of the post-vaccine serum #608 with a HAI titer of 320 was diluted 320-fold), and then subjected to a further 10-fold sub-dilution followed by the two-step triple serial sub-dilution (e.g., to 1 to 3200, 1 to 9600, and 1 to 28800, for the post-vaccination serum #608). The aliquots of diluted sera and labeled virus, 40 μL of each, were mixed in 96-well round bottom plates and incubated in the refrigerator (~4° C.) for 40 min. Then, 40-μL aliquots of diluted erythrocytes were added, thus making the final volumes 120 μL, and the plates were incubated for another 30 min on the bench at room temperature on an XY shaker with low shaking (~500 rpm). Then, the plates were centrifuged (400 g, 4 min), and the supernatant was discarded. The erythrocyte pellets were re-suspended in 120 μL of 1% HSA/PBS per well, and centrifuged again. The next wash was performed using 1% HSA/PBS containing 4.5 μg of TB, to stain erythrocytes and make them suitable for classification in the BioPlex bead array reader, in the manner described in Example 4 for MDCK cells. With this low-level staining, the classification region #1 of the bead array reader was used for reading the TB-stained erythrocytes. After the last wash, the erythrocytes were resuspended in the same staining solution, 100 μL per well, and the plate was read in the BioPlex reader. FIG. 17 shows typical results of the fADI titrations for the pre- and post-vaccination sera of donors #608 and #145. The fADI titration curves were fit to the standard sigmoidal titration curve to determine fADI subtiters, as described in Examples 7 and 8. The final fADI titers were found as products of the initial serum dilution and the found fADI sub-titer (e.g., for the post-vaccine serum #608, the final fADI titer was 320×26.7=8550.4).

Figure 18:
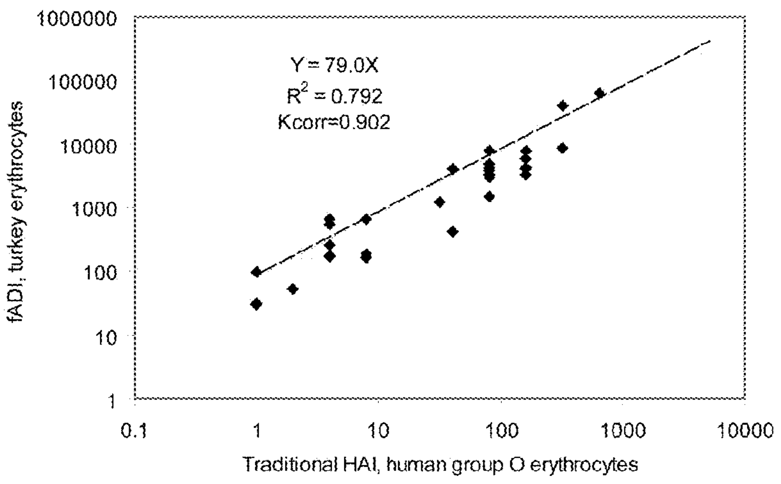
FIG. 18. Correlation of fADI titers and traditional HAI titers for the panel of human sera. Standard HAI experiments with human group O erythrocytes and BPL inactivated New Caledonia H1N1 virus. Turkey erythrocytes were used as target cells.

The fADI experiments with affinity-labeled New Caledonia H1N1 influenza virus and turkey erythrocytes described here were further performed for a panel of 36 pre- and post-vaccine donor sera. FIG. 18 demonstrates a good correlation between the classical HAI and fADI data, as well as an approximately 80-fold higher sensitivity of the fADI technique, as shown by the slope of the scatter plot.

Example 12 fADI Experiments Using Turkey Erythrocytes and Wisconsin H3N2 Influenza Virus

Figure 19:
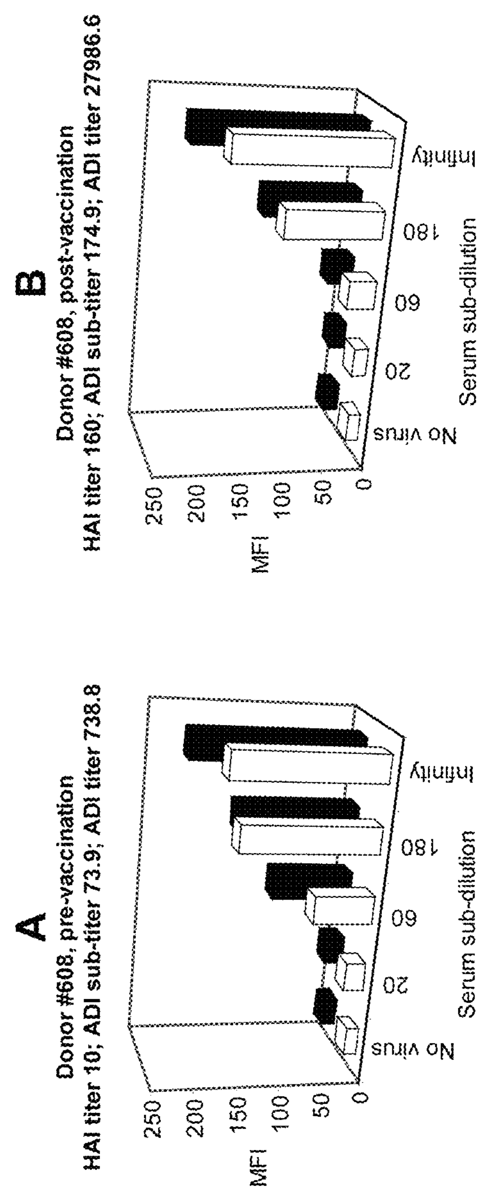
FIG. 19. Neutralizing capacity of human anti-influenza sera towards H3N2 virus, as determined using the fADI method and turkey erythrocytes as targets. Sera samples were pre-diluted according to their pre-determined HAI titers. The fADI titers shift upward after vaccination.

After successful testing with the H1N1 virus, the fADI technique with turkey erythrocytes was also examined with the H3N2 virus. The affinity fluorescent labeling was performed basically as described in Example 1 and Example 11 for Solomon Islands and New Caledonia H1N1 viruses, but using ViroStat anti-H3 biotinylated antibody #1317 instead of the anti-H1 #1307. Also, the final dilution of the virus was 400-fold rather than 3200-fold for the New Caledonia H1N1 virus, due to the weaker capacity of the Wisconsin H3N2 strain to adhere to target cells. Samples of the donor sera were diluted in 2% BSA/PBS to the levels of their previously determined HAI titers for the Wisconsin strain (e.g., the sample of the post-vaccination serum #608 having the HAI titer of 160 was diluted 160-fold), and then subjected to a further 20-fold sub-dilution, followed by two-step triple serial sub-dilution (e.g., to 1 to 3200, 1 to 9600 and 1 to 28800, for the post-vaccination serum #608). The rest of the experimental protocol was similar to that described in Example 11 above. FIG. 19 shows typical results of the fADI titrations for the pre- and post-vaccine sera of the donor #608.

Figure 20:
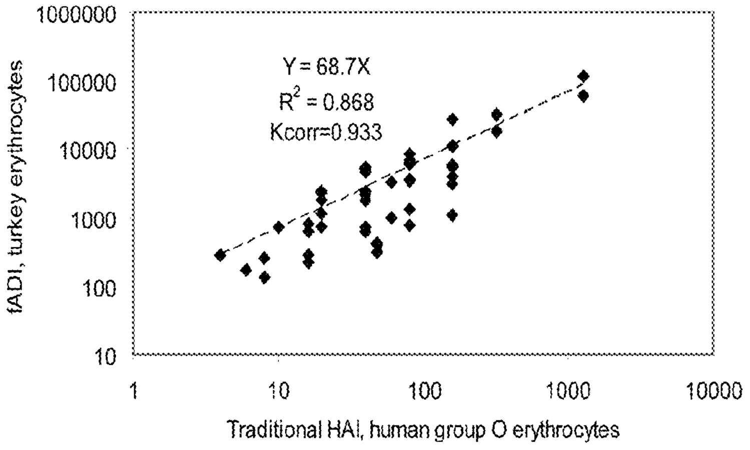
FIG. 20. Correlation of fADI titers and traditional HAI titers for the panel of human sera. Standard HAI experiments with human group O erythrocytes and BPL inactivated Wisconsin H3N2 virus. Affinity-labeled Wisconsin H3N2 BPL-inactivated virus; turkey erythrocytes were used as target cells.

The fADI experiments with affinity-labeled Wisconsin H3N2 BPL-inactivated influenza virus and turkey erythrocytes were further performed for a panel of 36 pre- and post-vaccination donor sera. FIG. 20 demonstrates the correlation between the HAI and fADI data, as well as an approximately 70-fold increased sensitivity of the fADI technique, compared with the classical HAI. Higher scattering of the data in the fADI versus HAI plot can be explained by altogether weaker binding and agglutinating capacity of the H3N2 virus, which resulted in less reliable titration in the traditional HAI assay.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method for determining a viral neutralizing activity of a test antibody, comprising:

a) incubating a test antibody with a fluorescently-labeled virus to form a mixture, b) incubating a population of target cells with the mixture of a) under conditions permitting endocytosis of the labeled virus by the target cells, c) incubating the population of target cells of b) with a quencher of fluorescence of the labeled virus bound to the surface of the cells, d) staining the population of target cells of c) with a dye, e) measuring fluorescence of labeled virus endocytozed by the target cells, and f) comparing the fluorescence measured in e) with fluorescence of fluorescently-labeled virus measured in a control experiment where the labeled virus was not incubated with a test antibody, thereby determining a neutralizing activity of a test antibody.

2. The method of claim 1, wherein the quencher of fluorescence of labeled virus bound to the surface of the cells is an antibody that specifically binds the fluorescent label of the labeled virus and wherein the antibody is conjugated to at least one quenching compound.

3. The method of claim 2, wherein the quenching compound conjugated to the antibody is a quenching dye.

4. The method of claim 3, wherein the quenching dye is quenching dye QSY-9 or quenching dye QSY-21.

5. The method of claim 1, wherein the dye staining the population of target cells is a dye that has a red and infrared fluorescence, thereby facilitating classification of the target cells in a bead array reader.

6. The method of claim 5, wherein the dye is trypan blue or crystal violet.

7. The method of claim 1, wherein the labeled virus comprises a virus selected from the group consisting of influenza viruses, adenoviruses, filoviruses, flaviviruses, herpesviruses, poxviruses, parvoviruses, reoviruses, picornaviruses, togaviruses, orthomyxoviruses, rhabdoviruses, retroviruses, and hepadnaviruses, conjugated to a fluorescent label.

8. The method of claim 1, wherein the labeled virus comprises a biotinylated virus selected from the group consisting of influenza viruses, adenoviruses, filoviruses, flaviviruses, herpesviruses, poxviruses, parvoviruses, reoviruses, picornaviruses, togaviruses, orthomyxoviruses, rhabdoviruses, retroviruses, and hepadnaviruses, conjugated to a streptavadin:fluorescent label.

9. The method of claim 1, wherein the labeled virus comprises a biotinylated virus selected from the group consisting of H1N1 influenza virus, H3N2 influenza virus, H5N1 influenza virus, Marburg hemorrhagic fever virus-like particles, and gamma-inactivated Ebola virus, conjugated to a streptavadin:fluorescent label.

10. The method of claim 1, wherein the virus is an inactivated or an attenuated virus.

11. The method of claim 1 wherein the virus is a virus inactivated using betapropiolactone (BPL) or UV or gamma irradiation.

12. The method of claim 1, where the population of target cells comprises a human cell line or avian erythrocytes.

13. The method of claim 1, where the population of target cells comprises Madin-Darby canine kidney epithelial cells or Vero green monkey kidney epithelial cells.

14. The method of claim 1, wherein the measuring is detecting the labeled virus using a flow cytometer or a bead array reader.

15. The method of claim 1, wherein the neutralizing activity of an antibody is blocking entry of the labeled virus into the target cells.

* * * * *